(12) United States Patent
Bohm et al.

(10) Patent No.: US 12,310,723 B2
(45) Date of Patent: May 27, 2025

(54) ADVANCED CONTINUOUS ANALYTE MONITORING SYSTEM

(71) Applicant: DexCom, Inc., San Diego, CA (US)

(72) Inventors: Sebastian Bohm, San Diego, CA (US); Mark Dervaes, Carlsbad, CA (US); Eric Johnson, San Marcos, CA (US); Apurv Ullas Kamath, San Diego, CA (US); Shawn Larvenz, Ramona, CA (US); Jacob S. Leach, San Diego, CA (US); Phong Lieu, San Diego, CA (US); Aarthi Mahalingam, San Diego, CA (US); Tom Miller, Valley Center, CA (US); Paul V. Neale, San Diego, CA (US); Jack Pryor, Ladera Ranch, CA (US); Thomas A. Peyser, Menlo Park, CA (US); Daiting Rong, San Diego, CA (US); Kenneth San Vicente, San Diego, CA (US); Mohammad Ali Shariati, Irvine, CA (US); Peter C. Simpson, Cardiff, CA (US); Matthew Wightlin, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 551 days.

(21) Appl. No.: 17/238,048

(22) Filed: Apr. 22, 2021

(65) Prior Publication Data

US 2021/0251531 A1 Aug. 19, 2021

Related U.S. Application Data

(63) Continuation of application No. 16/526,886, filed on Jul. 30, 2019, now Pat. No. 11,179,069, which is a
(Continued)

(51) Int. Cl.
A61B 5/145 (2006.01)
A61B 5/00 (2006.01)
(Continued)

(52) U.S. Cl.
CPC ........ *A61B 5/14532* (2013.01); *A61B 5/0002* (2013.01); *A61B 5/14503* (2013.01);
(Continued)

(58) Field of Classification Search
CPC ............ A61B 5/14532; A61B 5/14865; A61B 2560/0209; A61B 5/14503; A61B 5/145;
(Continued)

(56) References Cited

U.S. PATENT DOCUMENTS 5,016,631 A 5/1991 Hogrefe
5,742,389 A 4/1998 Zavislan et al.
(Continued)

FOREIGN PATENT DOCUMENTS

EP 1075209 A1 2/2001
EP 2621339 A4 3/2015
(Continued)

OTHER PUBLICATIONS

Communication Under Rule 71 (3) EPC—Intention To Grant, Mar. 1, 2019 for EP application No. 11833076, 113 pages.
(Continued)

Primary Examiner — Jennifer Robertson
Assistant Examiner — Karen E Toth
(74) Attorney, Agent, or Firm — Patterson + Sheridan, LLP

(57) ABSTRACT

The present invention relates generally to systems and methods for processing, transmitting, and displaying data received from continuous analyte sensor, such as a glucose sensor. In some embodiments, the continuous analyte sensor system comprises a sensor electronics module that includes
(Continued)

power saving features. One feature includes a low power measurement circuit that can be switched between a measurement mode and a low power mode, in which charging circuitry continues to apply power to electrodes of a sensor during the low power mode. In addition, the sensor electronics module can be switched between in a low power storage mode higher power operational mode via a switch. The switch can include a reed switch or optical switch, for example. A validation routine can also be implemented to ensure an interrupt signal sent from the switch is valid. The continuous analyte sensor can be physically connected to a sensor electronics module, which is in direct wireless communication with a plurality of different display devices.

11 Claims, 21 Drawing Sheets

Related U.S. Application Data continuation of application No. 16/259,930, filed on Jan. 28, 2019, now Pat. No. 10,687,740, which is a continuation of application No. 13/247,856, filed on Sep. 28, 2011, now Pat. No. 10,231,653.

(60) Provisional application No. 61/387,793, filed on Sep. 29, 2010.

(51) Int. Cl.
- A61B 5/1468 (2006.01)
- A61B 5/1486 (2006.01)
- G06F 1/3203 (2019.01)
- G06F 1/3287 (2019.01)
- G08C 17/02 (2006.01)

(52) U.S. Cl.
CPC .......... G06F 1/3203 (2013.01); G06F 1/3287 (2013.01); A61B 5/14507 (2013.01); A61B 5/1451 (2013.01); A61B 5/1468 (2013.01); A61B 5/14865 (2013.01); A61B 2560/0209 (2013.01); A61B 2560/0214 (2013.01); A61B 2562/02 (2013.01); G08C 17/02 (2013.01)

(58) Field of Classification Search
CPC ............... A61B 5/14507; G16H 40/60; A61M 2230/201; H01L 2924/301
See application file for complete search history.

(56) References Cited

U.S. PATENT DOCUMENTS

| | | | |
|---|---|---|---|
| 6,001,067 A | 12/1999 | Shults et al. | |
| 6,212,427 B1* | 4/2001 | Hoover | A61B 5/0006 600/515 |
| 6,424,847 B1 | 7/2002 | Mastrototaro et al. | |
| 6,477,395 B2 | 11/2002 | Schulman et al. | |
| 6,484,046 B1 | 11/2002 | Say et al. | |
| 6,512,939 B1 | 1/2003 | Colvin et al. | |
| 6,565,509 B1 | 5/2003 | Say et al. | |
| 6,579,690 B1 | 6/2003 | Bonnecaze et al. | |
| 6,925,105 B1 | 8/2005 | Partyka | |
| 6,931,327 B2 | 8/2005 | Goode, Jr. et al. | |
| 6,958,705 B2 | 10/2005 | Lebel et al. | |
| 7,239,896 B1 | 7/2007 | Hill et al. | |
| 7,295,226 B1 | 11/2007 | Meron et al. | |
| 7,310,544 B2 | 12/2007 | Brister et al. | |
| 7,756,561 B2 | 7/2010 | Reggiardo et al. | |
| 8,106,534 B2 | 1/2012 | Spurlin et al. | |
| 8,187,183 B2 | 5/2012 | Jin et al. | |
| 9,801,575 B2 | 10/2017 | Bohm et al. | |
| 10,231,653 B2 | 3/2019 | Bohm et al. | |
| 10,405,800 B2 | 9/2019 | Ganton et al. | |
| 10,656,695 B2 | 5/2020 | Cronin et al. | |
| 2002/0092612 A1 | 7/2002 | Davies et al. | |
| 2002/0120186 A1 | 8/2002 | Keimel | |
| 2003/0049004 A1 | 3/2003 | Cresens | |
| 2003/0162496 A1 | 8/2003 | Liu | |
| 2003/0187338 A1* | 10/2003 | Say | A61B 5/72 128/903 |
| 2004/0000713 A1 | 1/2004 | Yamashita et al. | |
| 2005/0027463 A1 | 2/2005 | Goode, Jr. et al. | |
| 2005/0043598 A1 | 2/2005 | Goode et al. | |
| 2005/0154271 A1 | 7/2005 | Rasdal et al. | |
| 2005/0182306 A1 | 8/2005 | Sloan | |
| 2005/0192557 A1 | 9/2005 | Brauker et al. | |
| 2005/0203360 A1 | 9/2005 | Brauker et al. | |
| 2005/0211755 A1 | 9/2005 | Peng | |
| 2005/0275547 A1 | 12/2005 | Kates | |
| 2006/0020187 A1 | 1/2006 | Brister et al. | |
| 2006/0220839 A1 | 10/2006 | Fifolt et al. | |
| 2006/0222566 A1 | 10/2006 | Brauker et al. | |
| 2006/0258929 A1 | 11/2006 | Goode, Jr. et al. | |
| 2007/0016381 A1 | 1/2007 | Kamath et al. | |
| 2007/0027385 A1 | 2/2007 | Brister et al. | |
| 2007/0032706 A1 | 2/2007 | Kamath et al. | |
| 2007/0078323 A1* | 4/2007 | Reggiardo | A61B 5/14546 600/347 |
| 2007/0138027 A1 | 6/2007 | Dinsmoor et al. | |
| 2007/0159235 A1* | 7/2007 | Fukui | H04Q 9/00 327/537 |
| 2007/0173712 A1* | 7/2007 | Shah | A61B 5/14532 73/1.01 |
| 2007/0197890 A1 | 8/2007 | Boock et al. | |
| 2007/0203966 A1 | 8/2007 | Brauker et al. | |
| 2007/0208245 A1 | 9/2007 | Brauker et al. | |
| 2007/0273333 A1 | 11/2007 | Andruk et al. | |
| 2008/0033254 A1 | 2/2008 | Kamath et al. | |
| 2008/0060952 A1 | 3/2008 | Negron | |
| 2008/0097908 A1 | 4/2008 | Dicks et al. | |
| 2008/0108942 A1 | 5/2008 | Brister et al. | |
| 2008/0119703 A1 | 5/2008 | Brister et al. | |
| 2008/0129486 A1 | 6/2008 | Jeckelmann et al. | |
| 2008/0154101 A1 | 6/2008 | Jain et al. | |
| 2008/0232604 A1 | 9/2008 | Dufresne et al. | |
| 2008/0278333 A1 | 11/2008 | Fennell et al. | |
| 2008/0281179 A1 | 11/2008 | Fennell et al. | |
| 2009/0076325 A1 | 3/2009 | Yokoi et al. | |
| 2009/0076360 A1 | 3/2009 | Brister et al. | |
| 2009/0120810 A1* | 5/2009 | Phan | A61B 5/1486 205/792 |
| 2009/0138207 A1 | 5/2009 | Cosentino et al. | |
| 2009/0146826 A1 | 6/2009 | Gofman et al. | |
| 2009/0163771 A1 | 6/2009 | Kimoto et al. | |
| 2009/0300616 A1 | 12/2009 | Sicurello et al. | |
| 2009/0318189 A1 | 12/2009 | Ben-David | |
| 2009/0318792 A1 | 12/2009 | Fennell et al. | |
| 2010/0099394 A1 | 4/2010 | Hainzl | |
| 2010/0160759 A1 | 6/2010 | Celentano et al. | |
| 2010/0185263 A1 | 7/2010 | Stevenson et al. | |
| 2010/0219351 A1 | 9/2010 | Roberts et al. | |
| 2010/0261513 A1 | 10/2010 | Izen et al. | |
| 2010/0277342 A1 | 11/2010 | Sicurello et al. | |
| 2010/0324382 A1* | 12/2010 | Cantwell | A61M 5/14244 600/316 |
| 2011/0054282 A1 | 3/2011 | Nekoomaram et al. | |
| 2011/0071365 A1 | 3/2011 | Lee et al. | |
| 2011/0099301 A1 | 4/2011 | Moallem et al. | |
| 2011/0105872 A1 | 5/2011 | Chickering, III et al. | |
| 2011/0208021 A1 | 8/2011 | Goodall et al. | |
| 2011/0263950 A1 | 10/2011 | Larson et al. | |
| 2011/0288388 A1 | 11/2011 | Shah et al. | |
| 2012/0078071 A1 | 3/2012 | Bohm et al. | |
| 2012/0172691 A1 | 7/2012 | Brauker et al. | |
| 2012/0265035 A1 | 10/2012 | Bohm et al. | |
| 2013/0137946 A1 | 5/2013 | Geske et al. | |
| 2013/0217979 A1 | 8/2013 | Blackadar et al. | |
| 2014/0266776 A1 | 9/2014 | Miller et al. | |
| 2015/0018643 A1 | 1/2015 | Cole et al. | |
| 2015/0119728 A1 | 4/2015 | Blackadar et al. | |
| 2015/0182153 A1 | 7/2015 | Feldman et al. | |

(56) References Cited

U.S. PATENT DOCUMENTS

| | | |
|---|---|---|
| 2016/0232318 A1 | 8/2016 | Mensinger et al. |
| 2017/0172472 A1 | 6/2017 | Wedekind et al. |
| 2017/0172473 A1 | 6/2017 | Wedekind et al. |
| 2018/0014787 A1 | 1/2018 | Ganton et al. |
| 2019/0129491 A1 | 5/2019 | Biederman, III et al. |
| 2019/0167169 A1 | 6/2019 | Bohm et al. |
| 2019/0328330 A1 | 10/2019 | Inan et al. |
| 2019/0336053 A1 | 11/2019 | Halac et al. |
| 2019/0342637 A1 | 11/2019 | Halac et al. |
| 2019/0350502 A1 | 11/2019 | Bohm et al. |
| 2022/0192545 A1 | 6/2022 | Halac et al. |
| 2024/0032826 A1 | 2/2024 | Bohm et al. |

FOREIGN PATENT DOCUMENTS

| | | |
|---|---|---|
| EP | 3787507 B1 | 12/2024 |
| JP | H03111754 A | 5/1991 |
| JP | 2000504599 A | 4/2000 |
| JP | 2009056311 A | 3/2009 |
| JP | 2015527093 A | 9/2015 |
| JP | 2018013970 A | 1/2018 |
| JP | 2018042715 A | 3/2018 |
| KR | 20080095266 A | 10/2008 |
| KR | 20100093575 A | 8/2010 |
| KR | 20140070486 A | 6/2014 |
| WO | WO-2006079114 A2 | 7/2006 |
| WO | WO-2007108517 A1 | 9/2007 |
| WO | WO-2009059203 A1 | 5/2009 |
| WO | WO-2009075696 A1 | 6/2009 |
| WO | WO-2010068617 A1 | 6/2010 |
| WO | 2019213319 A1 | 11/2019 |

OTHER PUBLICATIONS

Extended European Search Report for U.S. Appl. No. 11/833,076 mailed Feb. 4, 2015, 7 pages.

Extended European Search Report for Application No. 19195113.6, mailed Mar. 6, 2020, 6 pages.

File History U.S. Appl. No. 11/833,076 mailed Jul. 9, 2019, 529 pages.

International Preliminary Report on Patentability for Application No. PCT/US2011/053777 mailed Apr. 11, 2013, 6 pages.

International Search Report and Written Opinion for Application No. PCT/US2011/053777 mailed May 4, 2012, 7 pages.

Office Action from European Patent Application No. 19195113.6, dated Dec. 15, 2020, 4 pages.

International Search Report and Written opinion for Application No. PCT/US2019/030279 mailed Sep. 5, 2019, 14 pages.

\* cited by examiner

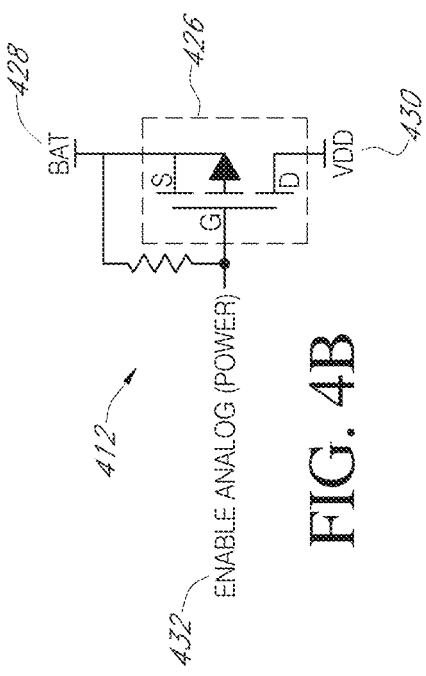
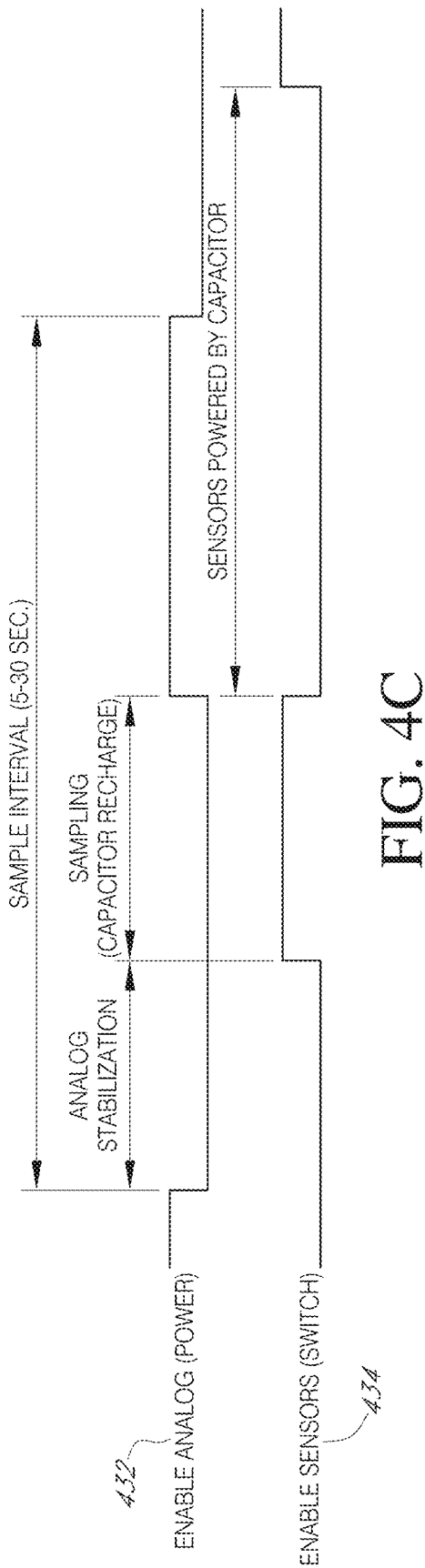
FIG. 4B
FIG. 4C

ADVANCED CONTINUOUS ANALYTE MONITORING SYSTEM

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/526,886, filed Jul. 30, 2019, which is a continuation of U.S. application Ser. No. 16/259,930, filed Jan. 28, 2019, now U.S. Pat. No. 10,687,740, which is a continuation of U.S. application Ser. No. 13/247,856, filed on Sep. 28, 2011, now U.S. Pat. No. 10,231,653, which claims the benefit of U.S. provisional application Ser. No. 61/387,793, filed Sep. 29, 2010. Each of the aforementioned applications is incorporated by reference herein in its entirety, and each is hereby expressly made a part of this specification.

FIELD OF THE INVENTION

The present invention relates generally to systems and methods for processing, transmitting and displaying data received from an analyte sensor, such as a glucose sensor.

BACKGROUND OF THE INVENTION

Diabetes mellitus is a disorder in which the pancreas cannot create sufficient insulin (Type 1 or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY OF THE INVENTION

Various implementations of systems, methods, and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect, a system is provided for continuous measurement of an analyte in a host, the system comprising: a continuous analyte sensor; and a sensor electronics module coupled to the sensor, the sensor electronics module comprising measurement circuitry, power circuitry, and charging circuitry, wherein the sensor electronics module is configured to switch between a first mode and a second mode, wherein in the first mode the power circuitry is coupled to the measurement circuitry and the charging circuitry, the measurement circuitry is coupled to the continuous analyte sensor, and the charging circuitry is decoupled from the continuous analyte sensor, and wherein in the second mode the power circuitry is decoupled from the measurement circuitry and the charging circuitry, the measurement circuitry is decoupled from the continuous analyte sensor, and the charging circuitry is coupled to the continuous analyte sensor.

In an embodiment of the first aspect, the sensor comprises a plurality of electrodes.

In an embodiment of the first aspect, the measurement circuitry applies a voltage across the electrodes of the sensor during the first mode and the charging circuitry applies a voltage across the electrodes of the sensor during the second mode.

In an embodiment of the first aspect, the system further comprises a second sensor, wherein in the first mode the measurement circuitry is coupled to the second sensor and the charging circuitry is decoupled from the second sensor, and wherein in the second mode the measurement circuitry is decoupled from the second sensor and the charging circuitry is coupled to the second sensor.

In a second aspect, a method is provided for switching between a measurement mode and a low power mode in a continuous analyte sensor, comprising: enabling power to measurement circuitry and charging circuitry; switching a reference capacitor to the charging circuit and the measurement circuitry to electrodes of a continuous analyte sensor; measuring an analyte concentration of a host using the continuous glucose sensor using the measurement circuitry; disabling power to the measurement circuitry and the charging circuitry; and switching the reference capacitor to the electrodes.

In a third aspect, a system is provided for continuous measurement of an analyte in a host, the system comprising: a continuous analyte sensor; and a sensor electronics module coupled to the continuous analyte sensor, the sensor electronics module comprising a switch configured to switch the sensor electronics module between a first low power mode and a second higher power mode.

In an embodiment of the third aspect, the switch is a reed switch.

In an embodiment of the third aspect, the switch is an optical switch.

In an embodiment of the third aspect, the switch is activated upon detection of movement of contacts of the sensor electronics module.

In an embodiment of the third aspect, the switch is configured to send an interrupt signal to a processor module of the electronics module to switch from the first mode to the second mode, and wherein the interrupt signal has a predetermined waveform.

In an embodiment of the third aspect, the processor module comprises a core processor and a statemachine, wherein the statemachine is configured to determine whether an interrupt waveform is valid.

In an embodiment of the third aspect, the system further comprises a mounting unit configured to hold a portion of the continuous analyte sensor, wherein the electronics module is configured to couple to the mounting unit, wherein the switch comprises split connectors configured to couple to the continuous analyte sensor when the electronics module is coupled to the mounting unit, and wherein the switch is configured to switch the sensor electronics module from the first mode to the second mode when the split connectors are coupled to the sensor.

In an embodiment of the third aspect, the split connectors are configured to couple to the sensor via contact pucks of the mounting unit when the electronics module is coupled to the mounting unit.

In an embodiment of the third aspect, the system further comprises a plurality of sensor electronics modules, wherein each of the sensor electronics modules is configured to be switched between a first low power mode and a second higher power mode.

In an embodiment of the third aspect, the sensor electronics module comprises a wireless receiver, and wherein the sensor electronics module is configured to be placed into the low power mode by receiving a predetermined signal via the wireless receiver.

In an embodiment of the third aspect, the switch is configured to switch from the first low power mode to the second higher power mode when the sensor electronics module detects a signal output of the sensor above a predetermined threshold.

In a fourth aspect, a method is provided for placing a sensor electronics module in a storage mode, the sensor electronics module comprising electronics configured to process and to transmit data from a continuous analyte sensor, the method comprising: receiving a predetermined storage mode command from an external telemetry device via a telemetry module of a sensor electronics module; initiating a storage mode using the sensor electronics module in response to receiving the predetermined storage mode command, wherein initiating the storage mode comprises initiating a routine to power down electronic components of the sensor electronics module; placing a switch of the sensor electronics module in a first state; monitoring, using circuitry of the sensor electronics module, for an interrupt signal from the switch; placing the switch in a second state; sending an interrupt signal in response to placing the switch in the second state; initiating a validation routine in response to receipt of the interrupt signal; and deactivating the storage mode if the validation routine indicates that the interrupt signal is valid, wherein deactivating the storage mode comprises initiating a routine to power up the electronic components of the sensor electronics module.

In an embodiment of the fourth aspect, the method is performed repeatedly.

In an embodiment of the fourth aspect, the switch is a reed switch, wherein placing the switch in the first state comprises placing a magnet in a proximity to the reed switch, and wherein placing the switch in the second state comprises removing the magnet from a proximity to the reed switch.

In an embodiment of the fourth aspect, the switch is an optical switch, and wherein placing the switch in the second state comprises removing a protective cover over the optical switch.

In an embodiment of the fourth aspect, the sensor electronics module is configured to not re-enter the storage mode after the sensor electronics module has been taken out of the storage mode.

In an embodiment of the fourth aspect, the storage mode command has a predetermined waveform.

In an embodiment of the fourth aspect, the interrupt signal has a predetermined waveform.

In an embodiment of the fourth aspect, the validation routine is performed using electronic circuitry that is separate from a processor of the sensor electronics module.

In an embodiment of the fourth aspect, the validation routine performs a plurality of iterative tests to determine if the interrupt signal is valid, wherein if one of the iterative tests fails, then no further iterative tests are performed on the interrupt signal and the validation routine is ended.

BRIEF DESCRIPTION OF THE DRAWINGS

FIG. 4B is a schematic diagram of power supply circuitry in accordance with one embodiment.

FIG. 4C is an exemplary timing diagram using low power measurement circuitry accordance with one embodiment.

DETAILED DESCRIPTION OF CERTAIN EMBODIMENTS

Figure 1:
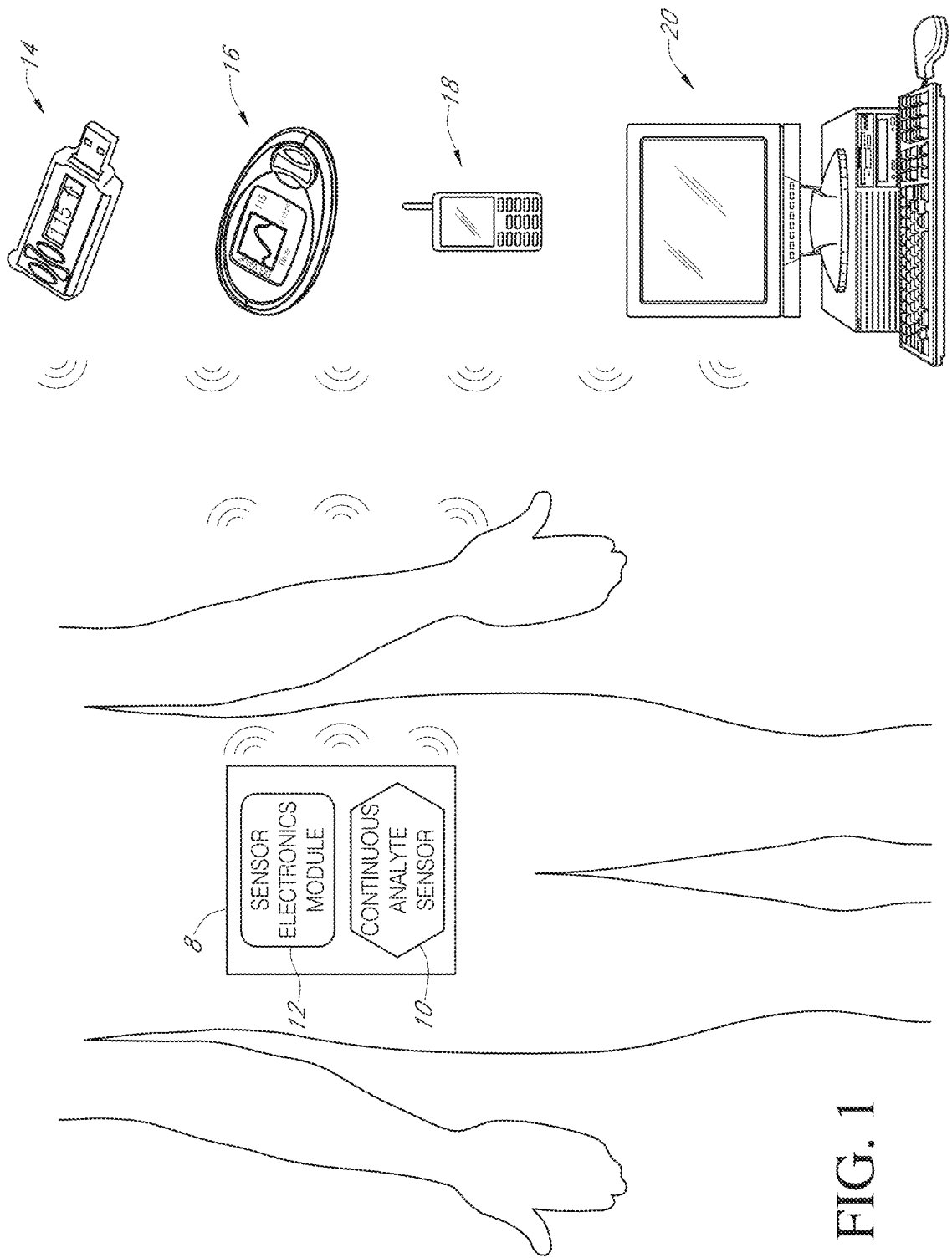
FIG. 1 is a schematic drawing of an architecture of a continuous analyte monitoring system including a sensor system in wireless communication with a plurality of display devices in accordance with one embodiment.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention. In addition, it should be understood that features of one embodiment described herein can be combined in another described embodiment and, thus, features described with respect to one embodiment should not be limited to only that described embodiment.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to acaboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphateuridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "calibration" as used herein is a broad term and is to be given its ordinary and customary meaning to a person of ordinary skill in the art (and is not to be limited to a special or customized meaning), and furthermore refers without limitation to a process of determining a relationship between a raw data stream and corresponding reference data, which can be used to convert raw data into calibrated data (defined below). In some embodiments, such as continuous analyte sensors, for example, calibration can be updated or recalibrated over time as changes in the relationship between the raw data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry. Thus, the output of a sensor may be an analog and/or digital signal. Examples of sensors include analyte sensors, glucose sensors, temperature sensors, altitude sensors, accelerometers, and heart rate sensors.

The terms "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "coupled", "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art (and are not to be limited to a special or customized meaning), and furthermore refers without limitation to one or more components that are connected to another component(s) through direct contact and/or a wired connection, including connecting via one or more intermediate physically connecting component(s). For example, a glucose sensor may be physically connected to a sensor electronics module, and thus the processor module located therein, either directly or via one or more electrical connections.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "continuous analyte sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer. In one embodiment, a glucose sensor performs continuous analyte sensing in order to monitor a glucose level in a corresponding host.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for a continuous analyte sensor, for example a self-monitoring blood glucose meter (SMBG) can be used as a reference for a continuous glucose sensor for comparison, calibration, and the like.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability may consider a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing). In instances where a sensor may need a period of time after initial implantation before the sensor provides reliable and accurate data (also referred to as a "break-in" period of time), the term "sensor session" can refer to a period of time starting at the time the sensor is considered broken-in to removal of the sensor.

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is substantially non-glucose related, such as interfering species, macro- or micro-motion, ischemia, pH changes, temperature changes, pressure, stress, or even unknown sources of mechanical, electrical and/or biochemical noise for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include sensor data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information may include reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, a calibration line drawn from the calibration set, in vitro parameters (e.g., sensor sensitivity), and/or a manufacturing code, for example.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, or tactile signal, triggered in response to one or more alarm conditions. In one embodiment, hyperglycemic and hypoglycemic alarms are triggered when present or predicted clinical danger is assessed based on continuous analyte data.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "sensor information" as used herein is a broad term, and is to be given its ordinary and customary meaning to a person of ordinary skill in the art (and is not to be limited to a special or customized meaning), and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art (and is not to be limited to a special or customized meaning), and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art (and is not to be limited to a special or customized meaning), and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art (and is not to be limited to a special or customized meaning), and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

The term "prospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in real-time (e.g., continuously and/or periodically as sensor data is received from the continuous analyte sensor) and provide real-time data output (e.g., continuously and/or periodically as sensor data is processed in the sensor electronics module).

The term "retrospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in retrospect, (e.g., analysis of a set of data for a time period previous to the present time period).

The terms "computer program product", "computer-readable medium", "software" and the like as used herein are broad terms, and are to be given their ordinary and customary meaning to a person of ordinary skill in the art (and are not to be limited to a special or customized meaning), and refer without limitation to media such as, memory storage devices, or storage unit. These, and other forms of computer-readable media, may be involved in storing one or more instructions for use by a processor to cause the processor to perform specified operations. Such instructions, generally referred to as "computer program code" (which may be grouped in the form of computer programs or other groupings), which when executed, enable a computing system to carry out specific functions in accordance with the computer program code.

As employed herein, the following abbreviations apply: Eq and Eqs (equivalents); mEq (milliequivalents); M (molar); mM (millimolar) μM (micromolar); N (Normal); mol (moles); mmol (millimoles); mol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. The sensor electronics module can include electronics configured to process a data stream associated with an analyte concentration measured by the continuous analyte sensor in order to generate displayable sensor information that includes raw sensor data, transformed sensor data, and/or any other sensor data, for example. The sensor electronics module can further be configured to generate displayable sensor information that is customized for respective display devices, such that different display devices may receive different displayable sensor information.

Alerts

In one embodiment, one or more alerts are associated with a sensor electronics module. For example, each alert can include one or more alert conditions that indicate when the respective alert has been triggered. For example, a hypoglycemic alert can include alert conditions indicating a minimum glucose level. The alert conditions can also be based on transformed sensor data, such as trending data, and/or sensor data from multiple different sensors (e.g. an alert may be based on sensor data from both a glucose sensor and a temperature sensor). For example, a hypoglycemic alert can include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend can indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions can include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data.

In one embodiment, multiple delivery actions (each having respective delivery options) can be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module need not be tied to a single display device, rather it can be configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. US-2007-0208246-A1, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), wherein the alarm mechanism is located on the display device.

In some embodiments, the sensor electronics module is configured to provide one or a plurality of different alarms via the sensor electronics module and/or via transmission of a data packaging indicating an alarm should be initiated by one or a plurality of display devices (e.g., sequentially and/or simultaneously). In some embodiments, the sensor electronics module determines which of the one or more alarms to trigger based on one or more alerts that are triggered. For example, when an alert triggers that indicates severe hypoglycemia, the sensor electronics module can perform multiple actions, such as activating an alarm on the sensor electronics module, transmitting a data package to a small (key fob) indicating activation of an alarm on the display, and transmitting a data package as a text message to a care provider. As an example, a text message can appear on a small (key fob) display, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, wherein the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, wherein the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house wherein the parents sleep at a distance from the child.

Display Devices

In some embodiments, the sensor electronics module is configured to search for and/or attempt wireless communication with a display device from a list of display devices. The sensor electronics module can be configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on. In one exemplary embodiment, the sensor electronics module is configured to search for and attempt to alarm a host or care provider sequentially using a list of display devices, such as: 1) a default display device, 2) a key fob device, 3) a cell phone (via auditory and/or visual methods, such as, text message to the host and/or care provider, voice message to the host and/or care provider, and/or 911).

In addition, one or more display devices that receive data packages from the sensor electronics module can be "dummy displays", wherein they display the displayable sensor information received from the sensor electronics module without additional processing (e.g., prospective algorithmic processing necessary for real-time display of sensor information). The displayable sensor information can comprise transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. The display device can be programmed with the display instructions at the manufacturer and can include security and/or authentication to avoid plagiarism of the display device. A display device can also be configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, personal digital assistants (PDAs), personal computers (PCs) and the like).

In some embodiments, certain display devices may be in direct wireless communication with the sensor electronics module, however intermediate network hardware, firmware, and/or software can be included within the direct wireless communication. A repeater (e.g., a Bluetooth repeater) can also be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In one embodiment, the sensor electronics module directly wirelessly transmits displayable sensor information to one or a plurality of display devices, such that the displayable sensor information transmitted from the sensor electronics module is received by the display device without intermediate processing of the displayable sensor information.

In one embodiment, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. However, any known authentication system or method useful for telemetry devices can be used with the preferred embodiments.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication No. US-2006-0222566-A1, U.S. Patent Publication No. US-2007-0203966-A1, U.S. Patent Publication No. US-2007-0208245-A1, and U.S. Patent Publication No. US-2005-0154271-A, each of which is incorporated herein by reference in its entirety, describe systems and methods for providing an integral reference analyte monitor incorporated into a display device and/or other calibration methods that can be implemented with the preferred embodiments.

In general, a plurality of display devices (e.g., a small (key fob) display device, a larger (hand-held) display device, a mobile phone, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Exemplary Configurations

FIG. 1 is a diagram illustrating one embodiment of a continuous analyte sensor system 8 including a sensor electronics module 12. In the embodiment of FIG. 1, the system includes a continuous analyte sensor 10 physically connected to a sensor electronics module 12, which is in direct wireless communication with a plurality of different display devices 14, 16, 18, and/or 20.

In one embodiment, the sensor electronics module 12 includes electronic circuitry associated with measuring and processing the continuous analyte sensor data, including prospective algorithms associated with processing and calibration of the sensor data. The sensor electronics module 12 may be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor, such as an analyte sensor. For example, the sensor electronics module 12 can include a potentiostat, a power source for providing power to the sensor, other components useful for signal processing and data storage, and preferably a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544, 6,931,327, U.S. Patent Publication No. US-2005-0043598-A1, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Patent Publication No. US-2005-0154271-A1, U.S. Patent Publication No. US-2005-0192557-A1, U.S. Patent Publication No. US-2006-0222566-A1, U.S. Patent Publication No. US-2007-0203966-A1 and U.S. Patent Publication No. US-2007-0208245-A1, each of which os incorporated herein by reference in its entirety.

Referring again to FIG. 1, a plurality of display devices (14, 16, 18, and/or 20) are configured for displaying (and/or alarming) the displayable sensor information that has been transmitted by the sensor electronics module 12 (e.g., in a customized data package that is transmitted to the display devices based on their respective preferences). For example, the display devices are configured to display the displayable sensor information as it is communicated from the sensor electronics module (e.g., in a data package that is transmitted to respective display devices), without any additional prospective processing required for calibration and real-time display of the sensor data. Transmitting displayable sensor information to a plurality of different display devices is discussed in more detail in U.S. Patent Publication No. US-2009-0240120-A1, the contents of which is incorporated herein by reference in its entirety.

In the embodiment of FIG. 1, the plurality of display devices includes a small (key fob) display device 14, such as a wrist watch, a belt, a necklace, a pendent, a piece of jewelry, an adhesive patch, a pager, a key fob, a plastic card (e.g., credit card), an identification (ID) card, and/or the like, wherein the small display device comprises a relatively small display (e.g., smaller than the large display device) and is configured to display certain types of displayable sensor information (e.g., a numerical value and an arrow, in some embodiments). In some embodiments, one of the plurality of display devices is a large (hand-held) display device 16, such as a hand-held receiver device, a palm-top computer and/or the like, wherein the large display device comprises a relatively larger display (e.g., larger than the small display device) and is configured to display a graphical representation of the continuous sensor data (e.g., including current and historic data). Other display devices can include other hand-held devices, such as a multi-functional mobile phone or PDA 18, an insulin delivery device, a blood glucose meter, and/or a desktop or laptop computer 20.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices are in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, a glucose sensor comprises a continuous sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In one embodiment, the analyte sensor is an implantable glucose sensor, such as described with reference to U.S. Pat. No. 6,001,067 and U.S. Patent Publication No. US-2005-0027463-A1. In another embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, U.S. Patent Publication No. US-2008-0119703-A1, U.S. Patent Publication No. US-2008-0108942-A1, and U.S. Pat. No. 7,828,728. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,12,939 to Colvin el al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Sensor Electronics Module

Figure 2A:
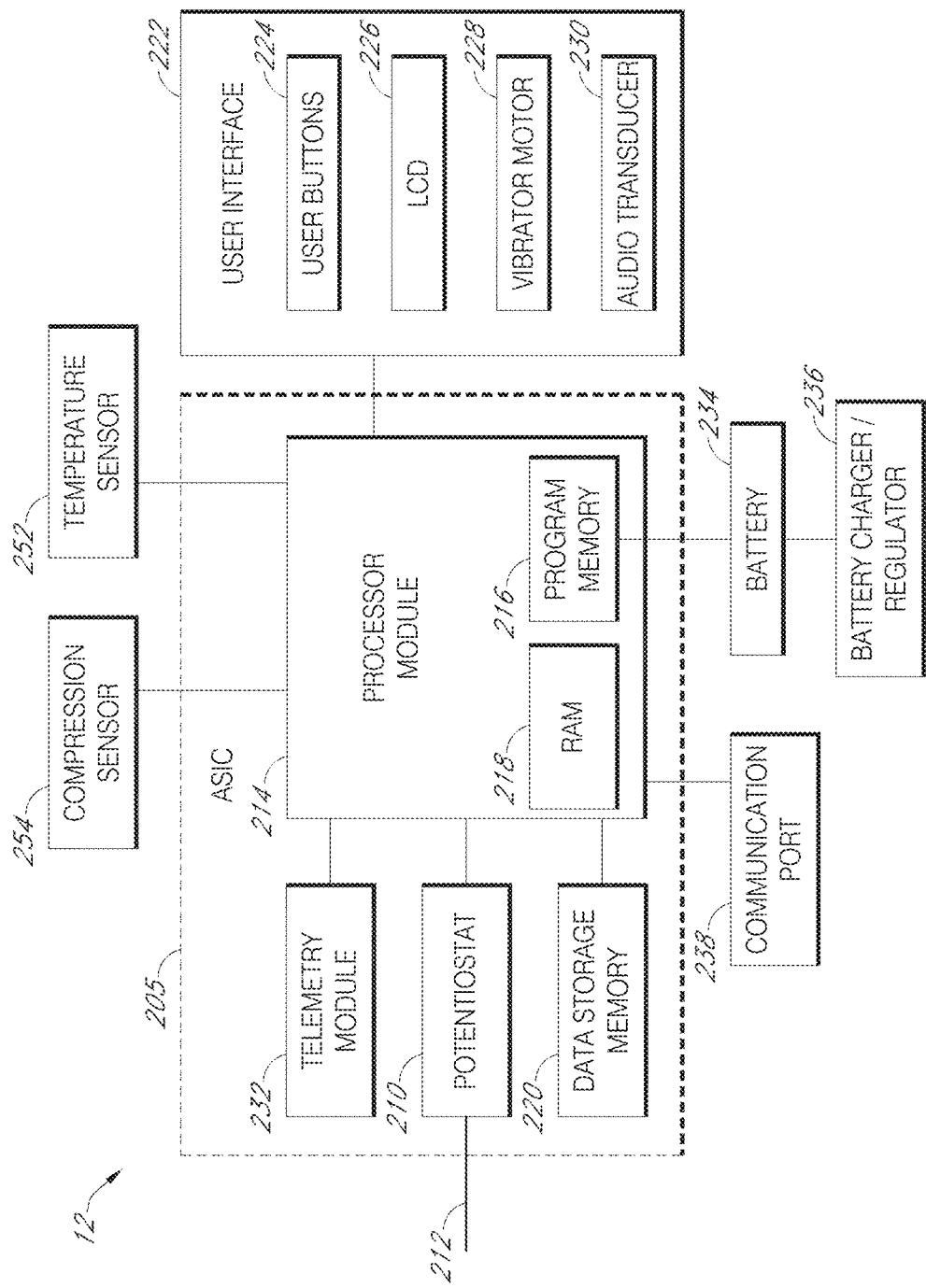
FIG. 2A is a block diagram of a sensor electronics module in accordance with one embodiment.

FIG. 2A is a block diagram illustrating one embodiment of the sensor electronics module 12 (FIG. 1). In the embodiment of FIG. 2A, the sensor electronics module 12 comprises an application-specific integrated circuit (ASIC) 205, a user interface 222, compression sensor 254 and temperature sensor 252. In this embodiment, the ASIC 205 is also coupled to a communication port 238 and a battery 234. Although the illustrated embodiment shows an ASIC 205 that includes much of the electronic circuitry, the ASIC 205 may be replaced with one or more of any suitable logic device, such as field programmable gate arrays (FPGA), microprocessors, analog circuitry, or other digital and/or analog circuitry. Further, ASIC 205 can include one or more additional features of sensor electronics module 12 discussed elsewhere herein, or one or more features illustrated in FIG. 2A as being part of the ASIC—such as telemetry module 232, potentiostat 210, data storage memory 220—can be separate from the ASIC.

In this embodiment, a potentiostat 210 is coupled to a glucose sensor via data line 212, for example, in order to receive sensor data from the glucose sensor. In one embodiment, the potentiostat 210 provides a voltage to the glucose sensor via a data line 212 in order to bias the sensor to enable measurement of a current value indicative of the analyte concentration in the host (also referred to as the analog portion). The potentiostat can have one channel or multiple channels (and a corresponding one or multiple data lines 212), depending on the number of working electrodes, for example. In some embodiments, the potentiostat 210 includes a resistor (not shown) that translates the current into voltage. In some embodiments, a current to frequency converter is provided that is configured to continuously integrate the measured current, for example, using a charge counting device. In some embodiments, an A/D converter digitizes the analog signal into "counts" for processing. Accordingly, the resulting raw data stream in counts is directly related to the current measured by the potentiostat 210.

A processor module 214 is the central control unit that controls the processing of the sensor electronics module 12. In some embodiments, the processor module 214 is formed as part of a custom chip, such as an ASIC, however a computer system other than an ASIC can be used to process data as described herein, for example a microprocessor can be used for some or all of the sensor electronics module processing. The processor module 214 typically provides a program memory 216, which provides semi-permanent storage of data, for example, storing data such as sensor identifier (ID) and programming to process data streams (for example, filtering, calibration, fail-safe checking, and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 218 can be used for the system's cache memory, for example for temporarily storing recent sensor data.

In some embodiments, the processor module 214 comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, such as when the potentiostat 210 is configured to measure the analyte at discrete time intervals, these time intervals determine the sample rate of the digital filter. In some alternative embodiments, wherein the potentiostat 210 is configured to continuously measure the analyte, for example, using a current-to-frequency converter, the processor module 214 can be programmed to request a digital value from the integrator at a predetermined time interval, also referred to as the acquisition time. In these alternative embodiments, the values obtained by the processor module 214 are advantageously averaged over the acquisition time due the continuity of the current measurement. Accordingly, the acquisition time determines the sample rate of the digital filter.

In an embodiment, the processor module 214 may be further configured to generate data packages for transmission to one or more display devices. Furthermore, the processor module 215 may generate data packets for transmission to these outside sources, e.g., via telemetry. As discussed above, the data packages may be customizable for each display device, for example, and may include any available data, such as displayable sensor information having customized sensor data and/or transformed sensor data, sensor/sensor electronics module ID code, raw data, filtered data, calibrated data, rate of change information, trend information, error detection or correction, and/or the like.

A data storage memory 220 is operably connected to the processor module 214 and is configured to store a variety of sensor information. In some embodiments, the data storage memory stores 1, 3, 4, 5, 6, 7, 8, 9, 10, 11, 12, 13, 14, 15, 20, 30 or more days of continuous analyte sensor data. In some embodiments, the data storage memory 220 stores sensor information such as raw sensor data (one or more raw analyte concentration values), calibrated data, filtered data, transformed sensor data, and/or any other displayable sensor information.

In some embodiments, sensor electronics module 12 is configured to receive and store contact information in the data storage memory (and/or program memory), including a phone number and/or email address for the sensor's host and/or health care providers for the host (e.g., family member(s), nurse(s), doctor(s), or other health care provider(s)), which enables communication with a contact person (e.g., via phone, pager and/or text messaging in response to an alarm (e.g., a hypoglycemic alarm that has not been responded to by the host)). In some embodiments, user parameters can be programmed into (and/or modified in) the data storage memory (and/or program memory) of the sensor electronics module, via a display device such as a personal computer, personal digital assistant, or the like. Preferably, user parameters include contact information, alert/alarms settings (e.g., thresholds, sounds, volume, and/or the like), calibration information, font size, display preferences, defaults (e.g., screens), and/or the like. Alternatively, the sensor electronics module can be configured for direct programming of certain user parameters.

In one embodiment, clinical data of a medical practitioner may be uploaded to the sensor electronics module 12 and stored on the data storage memory 220, for example. Thus, information regarding the host's condition, treatments, medications, etc., may be stored on the sensor electronics module 12 and may be viewable by the host or other authorized user. In one embodiment, certain of the clinical data may be included in a data package that is transmitted to a display device in response to triggering of an alert. The clinical data may be uploaded to the sensor electronics module 12 via any available communication protocol, such as direct transmission via a wireless Bluetooth, infrared, or RF connection, or via a wired USB connection, for example. Additionally, the clinical data may be uploaded to the sensor electronics module 12 via indirect transmission, such as via one or more networks (e.g., local area, personal area, or wide area networks, or the Internet) or via a repeater device that receives the clinical data from a device of the medical practitioner and retransmits the clinical data to the sensor electronics module.

Although separate data storage 220 and program memory 216 are shown in FIG. 2A, one skilled in the art appreciates a variety of configurations, including one or multiple memories that provide the necessary storage space to support the sensor electronic module 12 data processing and storage requirements. Accordingly, the described location of storage of any particular information and/or or programming is not meant to be limiting, but rather exemplary.

In some embodiments, the sensor electronics module 12 is configured to perform smoothing and/or filtering algorithms on the sensor data (e.g., raw data stream and/or other sensor information), wherein the smoothed and/or filtered data is stored in the data storage memory as transformed data. U.S. Patent Publication No. US-2005-0043598-A1, U.S. Patent Publication No. US-2007-0032706-A1, U.S. Patent Publication No. US-2007-0016381-A1 and U.S. Patent Publication No. US-2008-0033254-A1 describe some algorithms useful in performing data smoothing and/or filtering herein (including signal artifacts replacement), and are incorporated herein by reference in their entirety.

In some embodiments, the sensor electronics module 12 is configured to calibrate the sensor data, and the data storage memory 220 stores the calibrated sensor data points as transformed sensor data. In some further embodiments, the sensor electronics module 12 is configured to wirelessly receive calibration information from a display device, from which the sensor electronics module is configured to calibrate the sensor data. U.S. Pat. Nos. 7,310,544 and 6,931,327 describe some algorithms useful in sensor calibration herein, and are incorporated herein by reference in their entirety.

In some embodiments, the sensor electronics module 12 is configured to perform additional algorithmic processing on the sensor data (e.g., calibrated and/or filtered data and/or other sensor information) and the data storage memory 220 is configured to store the transformed sensor data and/or sensor diagnostic information associated with the algorithms. U.S. Pat. Nos. 7,310,544 and 6,931,327 describe some algorithms that can be processed by the sensor electronics module, and are incorporated herein by reference in their entirety.

Referring again to FIG. 2A, a user interface 222 can include a variety of interfaces, such as one or more buttons 224, a liquid crystal display (LCD) 226, a vibrator 228, an audio transducer (e.g., speaker) 230, backlight, and/or the like. A backlight can be provided, for example, to aid the user in reading the LCD in low light conditions. The components that comprise the user interface 222 provide controls to interact with the user (e.g., the host). One or more buttons 224 can allow, for example, toggle, menu selection, option selection, status selection, yes/no response to on-screen questions, a "turn off" function (e.g., for an alarm), a "snooze" function (e.g., for an alarm), a reset, and/or the like. The LCD 226 can be provided, for example, to provide the user with visual data output. The audio transducer 230 (e.g., speaker) provides audible signals in response to triggering of certain alerts, such as present and/or predicted hyper- and hypoglycemic conditions. In some embodiments, audible signals are differentiated by tone, volume, duty cycle, pattern, duration, and/or the like. In some embodiments, the audible signal is configured to be silenced (e.g., snoozed or turned off) by pressing one or more buttons 224 on the sensor electronics module and/or by signaling the sensor electronics module using a button or selection on a display device (e.g., key fob, cell phone, and/or the like).

A telemetry module 232 is operably connected to the processor module 214 and provides the hardware, firmware, and/or software that enable wireless communication between the sensor electronics module 12 and one or more display devices. A variety of wireless communication technologies that can be implemented in the telemetry module 232 include radio frequency (RF), infrared (IR), Bluetooth, spread spectrum communication, frequency hopping communication, ZigBee, IEEE 802.11/802.16, wireless (e.g., cellular) telecommunication, paging network communication, magnetic induction, satellite data communication, GPRS, ANT, and/or the like. In one preferred embodiment, the telemetry module comprises a Bluetooth chip. In some embodiments, Bluetooth technology is implemented in a combination of the telemetry module 232 and the processor module 214.

A battery 234 is operatively connected to the processor module 214 (and possibly other components of the sensor electronics module 12) and provides the necessary power for the sensor electronics module 12. In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example.

A battery charger and/or regulator 236 may be configured to receive energy from an internal and/or external charger. In one embodiment, a battery regulator (or balancer) 236 regulates the recharging process by bleeding off excess charge current to allow all cells or batteries in the sensor electronics module to be fully charged without overcharging other cells or batteries. In some embodiments, the battery 234 (or batteries) is configured to be charged via an inductive and/or wireless charging pad. One skilled in the art appreciates a variety of known methods of charging batteries, which can be implemented with the system described herein, including wired (cable/plug) and wireless methods.

One or more communication ports 238, also referred to as external connector(s), can be provided to allow communication with other devices, for example a PC communication (com) port can be provided to enable communication with systems that are separate from, or integral with, the sensor electronics module. The communication port, for example, may comprise a serial (e.g., universal serial bus or "USB") communication port, allows for communicating with another computer system (e.g., PC, smart mobile phone, personal digital assistant or "PDA," server, or the like). In one exemplary embodiment, the sensor electronics module 12 is able to transmit historical data to a separate computing device for retrospective analysis by a patient and/or physician.

In conventional continuous analyte sensor systems, the on-skin portion of the sensor electronics is generally simplified to minimize complexity and/or size of on-skin electronics, for example, providing only raw, calibrated, and/or filtered data to a secondary display device configured to run calibration and other algorithms required for displaying the sensor data. In contrast, the sensor electronics module 12 executes prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like, which are described in more detail in U.S. Pat. Nos. 7,310,544, 6,931,327, U.S. Patent Publication No. US-2005-0043598-A1, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Patent Publication No. US-2005-0154271-A1, U.S. Patent Publication No. US-2005-0192557-A1, U.S. Patent Publication No. US-2006-0222566-A1, U.S. Patent Publication No. US-2007-0203966-A1 and U.S. Patent Publication No. US-2007-0208245-A1, each of which is incorporated herein by reference in its entirety. Furthermore, the sensor electronics module 12 is configured to store the transformed sensor data (e.g., values, trend information) and to communicate the displayable sensor information to a plurality of different display devices. In some embodiments, the display devices are "dummy" devices, namely, they are configured to display the displayable sensor information as received from the sensor electronics module 12, without any additional sensor data processing.

Figure 2B:
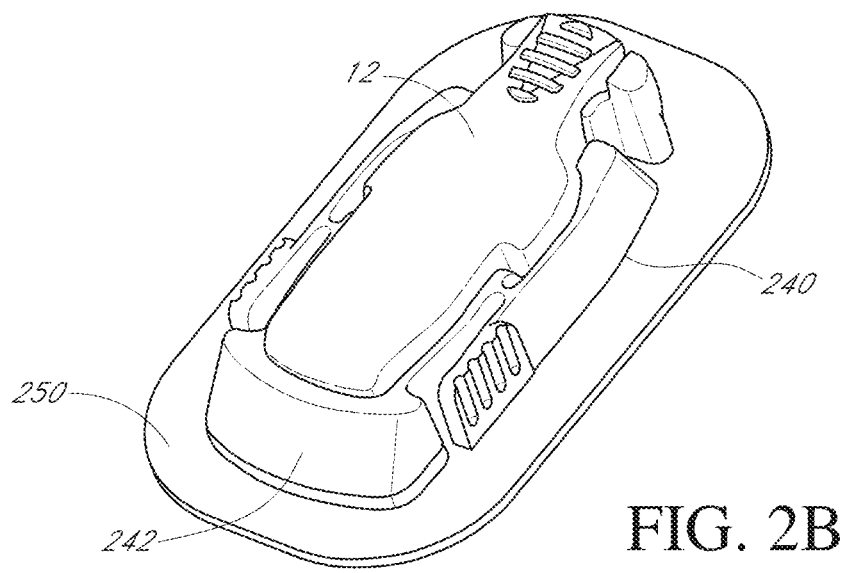
FIG. 2B is a perspective view of the sensor electronics module of FIG. 2A held in a mounting unit in accordance with one embodiment.
Figure 2C:
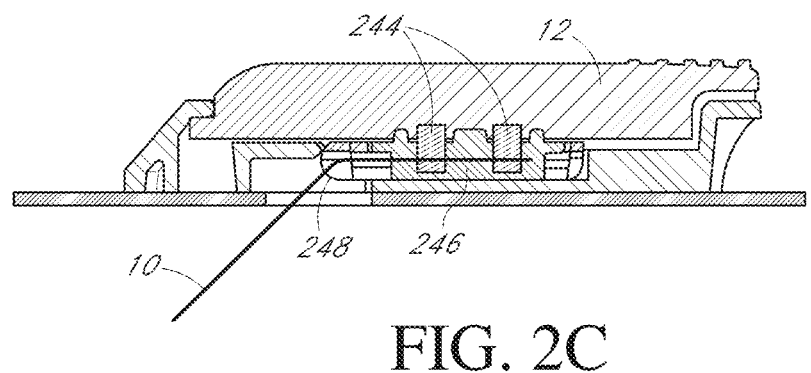
FIG. 2C is a side cross-sectional view of the sensor electronics module and mounting unit of FIG. 2B in accordance with one embodiment.

FIGS. 2B and 2C are perspective and side views of a sensor system including a mounting unit 240 and sensor electronics module 12 attached thereto in one embodiment, shown in its functional position, including a mounting unit and a sensor electronics module matingly engaged therein. In some preferred embodiments, the mounting unit 240, also referred to as a housing or sensor pod, comprises a base 242 adapted for fastening to a host's skin. The base 242 can be formed from a variety of hard or soft materials, and preferably comprises a low profile for minimizing protrusion of the device from the host during use. In some embodiments, the base 242 is formed at least partially from a flexible material, which is believed to provide numerous advantages over conventional transcutaneous sensors, which, unfortunately, can suffer from motion-related artifacts associated with the host's movement when the host is using the device. The mounting unit 240 and/or sensor electronics module 12 can be located over the sensor insertion site to protect the site and/or provide a minimal footprint (utilization of surface area of the host's skin).

In some embodiments, a detachable connection between the mounting unit 240 and sensor electronics module 12 is provided, which enables improved manufacturability, namely, the relatively inexpensive mounting unit 240 can be disposed of when replacing the sensor system after its usable life, while the relatively more expensive sensor electronics module 12 can be reusable with multiple sensor systems. In some preferred embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 244 are mounted on or in a subassembly hereinafter referred to as a contact subassembly 246 configured to fit within the base 242 of the mounting unit 240 and a hinge 248 that allows the contact subassembly 246 to pivot between a first position (for insertion) and a second position (for use) relative to the mounting unit 240. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 244 are formed from a conductive elastomeric material, such as a carbon black elastomer, through which the sensor 10 extends.

In certain embodiments, the mounting unit 240 is provided with an adhesive pad 250, disposed on the mounting unit's back surface and including a releasable backing layer. Thus, removing the backing layer and pressing the base portion 242 of the mounting unit 240 onto the host's skin adheres the mounting unit to the host's skin. Additionally or alternatively, an adhesive pad 240 can be placed over some or all of the sensor system 8 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2B and 2C are described in more detail with reference to U.S. Pat. No. 7,310,544, which is incorporated herein by reference in its entirety. Preferably, configurations and arrangements that provide water resistant, waterproof, and/or hermetically sealed properties are provided associated with the mounting unit/sensor electronics module embodiments described herein.

Low Power Measurement Circuit

Some embodiments of sensor system 8 utilize a low power measurement circuit that is capable of switching between a measurement mode and a low power mode to conserve power usage. During the measurement mode, measurement circuitry can be powered and electrically coupled to sensor electrodes to take sensor measurements. Also during the measurement mode, a charging circuit can be powered and electrically coupled to a capacitive circuit to charge the capacitive circuit. After a measurement is complete, the circuit can enter the low power mode. In the low power mode, the measurement circuitry can be decoupled from the sensor electrodes and powered down, and the charging circuitry can be decoupled from the capacitive circuit and powered down. In addition, during the low power mode, the capacitive circuit can be electrically coupled to the sensor electrode or sensor electrodes to maintain a voltage across the electrode(s). In this way, measurement circuitry can be powered down in between taking measurements to reduce power consumption, but yet a voltage can be maintained across the sensor electrodes through the use of capacitive circuit. Maintaining a voltage across the sensor electrodes while measurement circuitry is powered down may be desired, depending upon the sensor configuration, to maintain sensor electrochemistry, for example.

Figure 3:
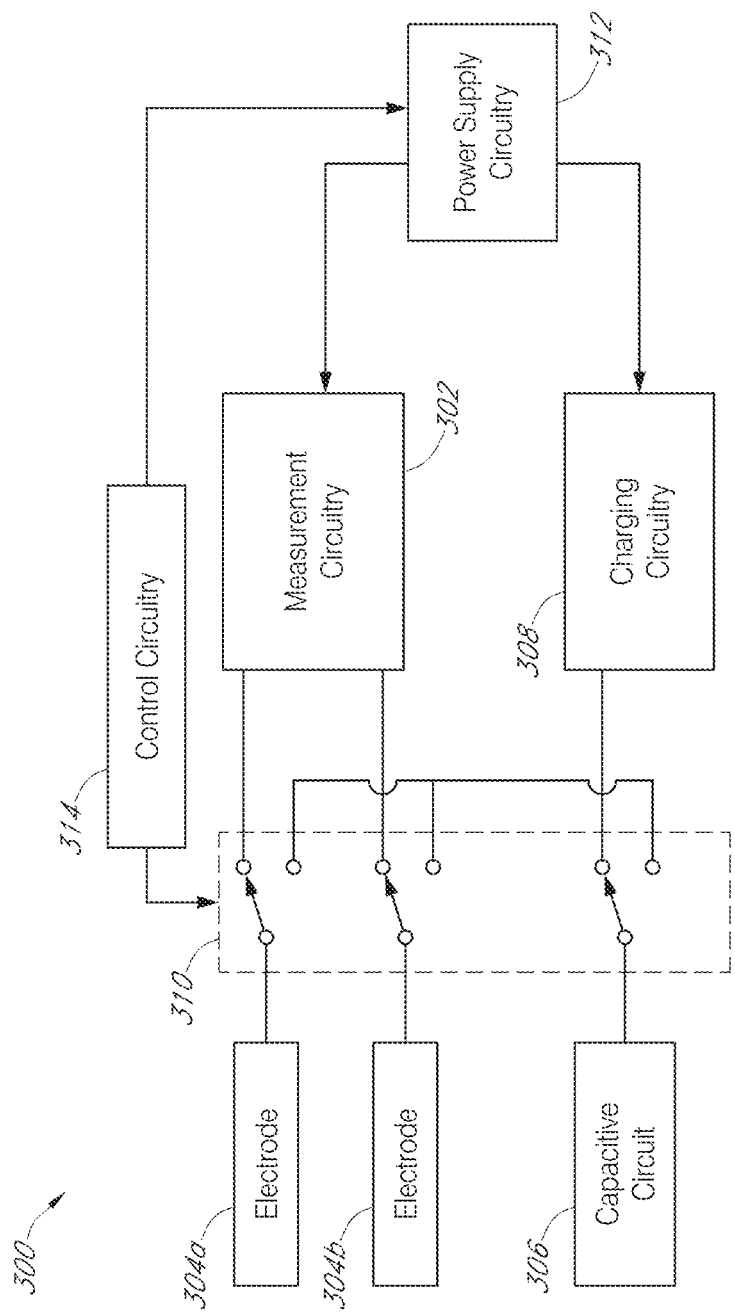
FIG. 3 is a schematic block diagram of low power measurement circuit in accordance with one embodiment.

Reference is now made to FIG. 3, which is a simplified block diagram of an embodiment of a low power potentiostat circuit 300. Low power potentiostat circuit 300 can include measurement circuitry 302, sensor electrodes 304a and 304b, capacitive circuitry 306 and charging circuitry 308. Also illustrated is switch 310 configured to switch sensor electrodes 304a and 304b between measurement circuitry 302 and capacitive circuitry 306. Switch 310 is also configured to switch capacitive circuitry 306 between sensor electrodes 304a and 304b and charging circuitry 308. That is, when switch 310 is in a first state, electrodes 304a and 304b are connected to measurement circuitry 302 and capacitive circuitry 306 is connected to charging circuitry 308. When switch 310 is in a second state, sensor electrodes 304a and 304b are connected to capacitive circuitry 306. In FIG. 3, switch 310 is a three-way double-throw switch; however, other suitable switches can be used instead, such as three individual switches in place of one switch and the like.

Also illustrated in FIG. 3 is power circuitry 312 and control circuitry 314. Power circuitry 312 is configured to selectively provide power to measurement circuitry 302 and charging circuitry 308, which in turn can sense outputs of electrodes 304a and 304b, and drive capacitive circuitry 306, respectively. Control circuitry 314 is configured to selectively enable power circuitry 312 and selectively enable switch 310 between its various states. Power circuitry 312 can include any suitable power supply source, such as a rechargeable, replaceable or disposable battery. Power circuitry 312 can also include any other circuitry needed to convert the power source into a suitable voltage source to power the components of circuit 300. Control circuitry 314 can be implemented via an ASIC or a general purpose processor, for example.

Low power potentiostat circuit 300 can power down measurement circuitry 302 while maintaining sensor electrode voltage/current through the use of capacitive circuitry 306. To illustrate, when obtaining a measurement using sensor electrodes 304a and 304b, switch 310 is in the first state (e.g. a measurement mode) so as to electrically connect sensor electrodes 304a and 304b with measurement circuitry 302 and power circuitry 312. Also, while switch 310 is in the first state, capacitive circuitry 306 is electrically connected to charging circuitry 308 and power circuitry 312, resulting in charging of the capacitive circuitry 306. After the measurement is performed, switch 310 switches to the second state (e.g., a low power mode), connecting sensor electrodes 304a and 304b to capacitive circuitry 306. Further, while in the second state, capacitive circuitry 306 supplies power to sensor electrodes 304a and 304b. Thus, the power supply circuitry 312 supplies power to sensor electrodes 304a and 304b and charges capacitive circuitry 306 while in the first state. Capacitive circuitry 306 then supplies power to sensor electrodes 304a and 304b while in the second state.

It is appreciated that, although FIG. 3 illustrates two sensor electrodes 304a and 304b, low power potentiostat circuit 300 can include any number of sensor electrodes, such as one, two, three or more sensor electrodes. Further, in some embodiments, one or more of a plurality of sensor electrodes can be in the first state while the remaining sensor electrodes of the plurality of sensor electrodes are in the second state. Indeed, in some embodiments, some or all of a plurality of electrodes 304 can be selectively switched between the first and second state independently from other electrodes included in the measurement circuitry 302.

Figure 4A:
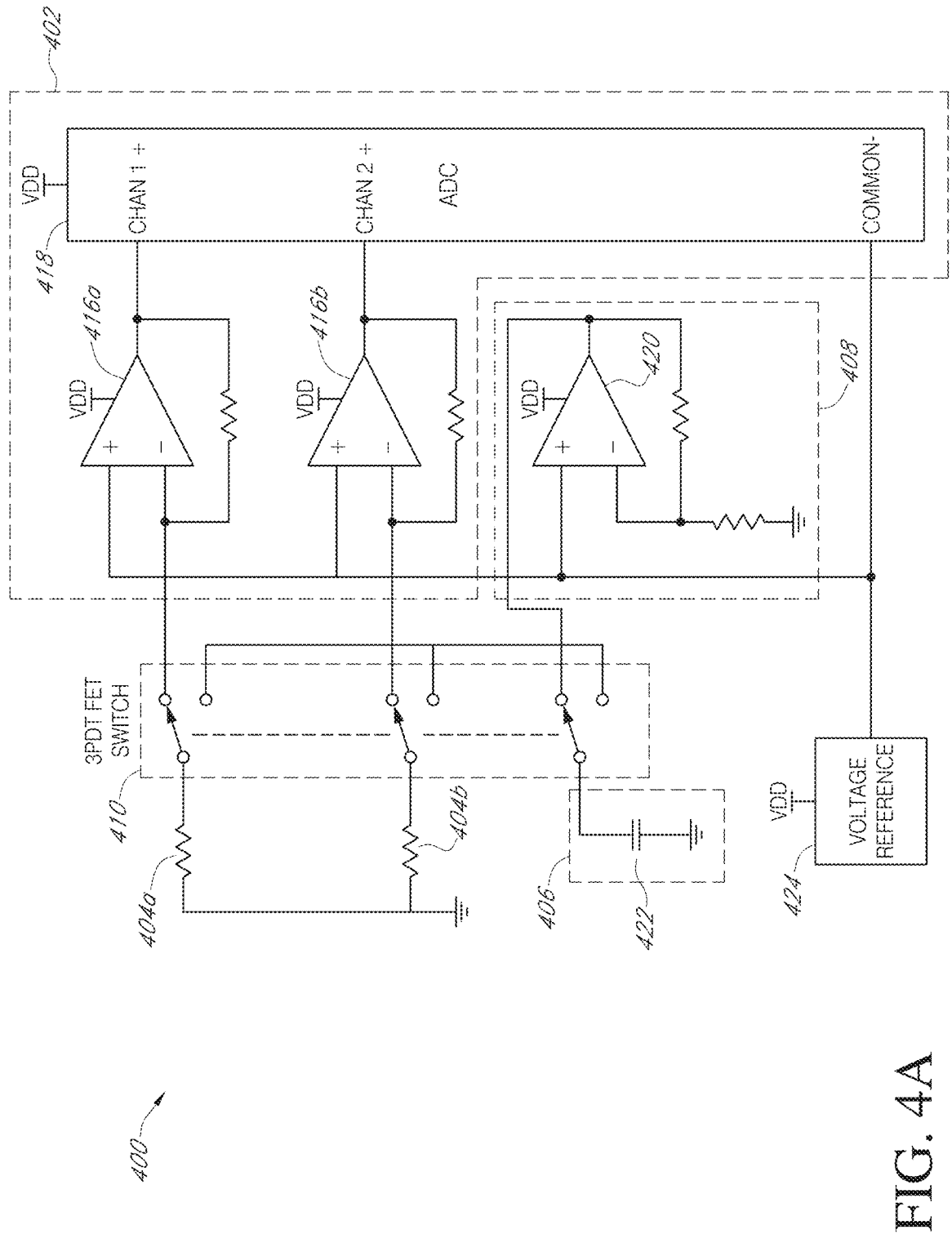
FIG. 4A is a schematic circuit diagram of a low power measurement circuit in accordance with one embodiment.

Reference is now made to FIG. 4A, which is a schematic circuit diagram of one embodiment of a low power potentiostat circuit 400. Low power potentiostat circuit 400 has measurement circuitry 402 that includes operational amplifiers 416a and 416b connected to separate channels of A/D converter 418. Charging circuitry 408 of circuit 400 includes a reference capacitor charge amplifier 420, which can be set above a reference voltage as discussed more below, and capacitive circuit 406 can include a reference capacitor 422. Voltage reference block 424 is electrically connected to each of operational amplifiers 416a and 416b, A/D converter 418 and charge amplifier 420 for supplying a reference voltage thereto.

Further to FIG. 4A, switch 410, which can be implemented as a three-pole double-throw field effect transistor (3DPT FET), is configured to switch electrodes 404a and 404b between measurement circuitry 402 and capacitive circuitry 406. Likewise, switch 410 connects capacitive circuitry 406 with charging circuitry 408 when capacitive circuitry 406 is not connected to electrodes 404a and 404b.

In some embodiments, reference capacitor 422 is selected to provide a greater charge than reference voltage 424 when fully charged. A reason for doing so can be because a voltage supplied by a capacitor can diminish as the capacitor discharges. To illustrate, providing a reference capacitor that initially supplies a voltage about equal to the voltage of the voltage supplied by reference voltage block 424 can result in capacitive circuit 406 providing insufficient voltage later on, because the capacitor discharges when it is not being charged; for example, during the low power mode. Thus, selecting a reference capacitor 422 with an appropriately large voltage rating can supply a voltage to electrodes 404a and 404b that is greater than the reference voltage during the duration of the low power mode, even though the voltage supplied by the capacitor may be decreasing as the low power mode transpires. For at least this reason, some embodiments select a reference capacitor 422 that provides a voltage greater than the reference voltage during the entire low power mode to take into account any voltage change supplied by capacitor due to the capacitor discharging during a low power mode.

In addition, in instances where the voltage supplied by the reference capacitor 422 need not be above the reference voltage during the entire low power mode, some embodiments select a reference capacitor 422 that provides a voltage that stays within a predetermined range of the reference voltage during the entire low power mode. For example, reference capacitor 422 can be selected to provide a voltage that is within 1%, 5%, 10% or 20% of the reference voltage during the entire low power mode.

In one embodiment, reference capacitor 422 is sized for a 1% change over a low power mode interval. Further, the reference capacitor charge amplifier 420 can be set to 0.5% above the reference voltage.

FIG. 4B is a schematic diagram of power supply circuitry 412 that can be used with circuit 400 of FIG. 4A to selectively enable (e.g., turn on) and disable (e.g. turn off) power to measurement circuitry 402 and charging circuitry 408. Power supply circuitry 412 includes p-type MOSFET 426 that is configured to supply battery 428 voltage to terminals (VDD) of the various components of circuit 400

(such as operational amplifiers 416a, 416b and 420, A/D converter 418 and voltage reference 424) upon receipt of enable signal 432. MOSFET 426 is also configured to discontinue supplying voltage upon receipt of a disable signal, which can simply be a discontinuation of the enable signal.

FIG. 4C is an exemplary timing diagram of low power potentiostat circuit 400. Note that the timing diagram of FIG. 4C is not necessary drawn to scale. In general, the low power potentiostat circuit 400 can be controlled by a microprocessor that generates power signal 432 and switch signal 434. When awakened from a low power sleep mode, the microprocessor can enable power (indicated by falling edge of power signal 434), which switches on MOSFET 426, to provide power to measurement circuitry 402 and charging circuitry 408. This starts a measurement interval, which can last from 5 to 30 seconds, for example. Note that at this time reference capacitor 422 is not yet switched out of circuit 400 to allow reference amplifier 420 and operational amplifiers 416a and 416b time to stabilize.

After a period of time that allows for stabilization (also referred to as "stabilization time period") of measurement circuitry 402 and charging circuitry 408, the microprocessor enables switch 410 via switch signal 434 (indicated by the rising edge of switch signal 434). This switches reference capacitor 422 to charge circuit 408 and the measurement circuitry 402 to sensor electrodes 404a and 404b. Although not indicated in the timing diagram, a second stabilization time period can then be provided before measurement takes place.

Once the measurement is complete and reference capacitor 422 recharged, the microprocessor disables power (indicated by rising edge of power signal 432) and enables switch (indicated by falling edge of sensor enable signal 434). This causes sensor electrodes 404a and 404b to switch back to reference capacitor 422 and measurement circuitry 402 and charging circuitry 408 to power down by switching off MOSFET 426.

In non-limiting examples, a sample interval can last in the range of 5 to 30 seconds. A sample interval can include measurement, stabilization and capacitive powering time periods. Further, the stabilization period can last in the range of 10 to 20 ms to stabilize the circuitry and the measurement period can last approximately 10 ms. This can provide for a duty cycle, depending upon the timing, of less than 1%, thereby significantly reducing power consumption.

Low Power Storage Mode and Sensor System Kit

Consuming power while electronic components, such as those in sensor electronics module 12 (FIG. 2A), are not in normal use—such as while in storage prior to use—can drain valuable battery power; particularly if, for example, battery 234 is a non-rechargeable and/or non-replaceable type of battery. Indeed, the amount of power available to sensor electronics module 12 can be a limiting factor as to the life of sensor electronics module and/or what features can be incorporated into sensor electronics module. Thus, the amount of power consumed by sensor electronics module 12 while in storage can not only limit its useful life, but can also limit its capabilities.

Some embodiments reduce the amount of power consumed by sensor electronics module 12 by putting sensor electronics module in a power saving storage mode while it is in storage. In general, a storage mode can be activated with a command at manufacturing that initiates a routine implemented by software stored in program memory 216, for example, to power off select circuitry in sensor electronics module 12 and put processor module 214 into a low power mode (e.g., sleep mode). Sensor electronics module 12 can then be placed in a package that places sensor electronics module 12 next to a storage magnet, which keeps it in storage mode until sensor electronics module 12 is pulled away from the magnet by a user. The storage magnet can be incorporated into the packaging directly next to where the sensor electronics module 12 is held, for example.

In some embodiments, pulling a magnet away from sensor electronics module switches sensor electronics module 12 out of a storage mode and into a normal operation mode. For example, pulling the sensor electronics module 12 away from the magnet can trigger an interrupt line, which initiates an interrupt routine performed by software stored in the electronics module 12. Once started, the interrupt routine can initiate a state machine implemented using sleep timer interrupts which check periodically across multiple intervals, for a predetermined amount of time, such as five minutes, to validate that the sensor electronics module 12 has indeed been moved away from the magnet. Once the state machine concludes that the storage magnet has been removed, the state machine puts sensor electronics module 12 in normal operation mode by, for example, pulling processor 214 out of low power mode, and restoring or providing power to other circuitry of sensor electronic module 12.

Figure 5A:
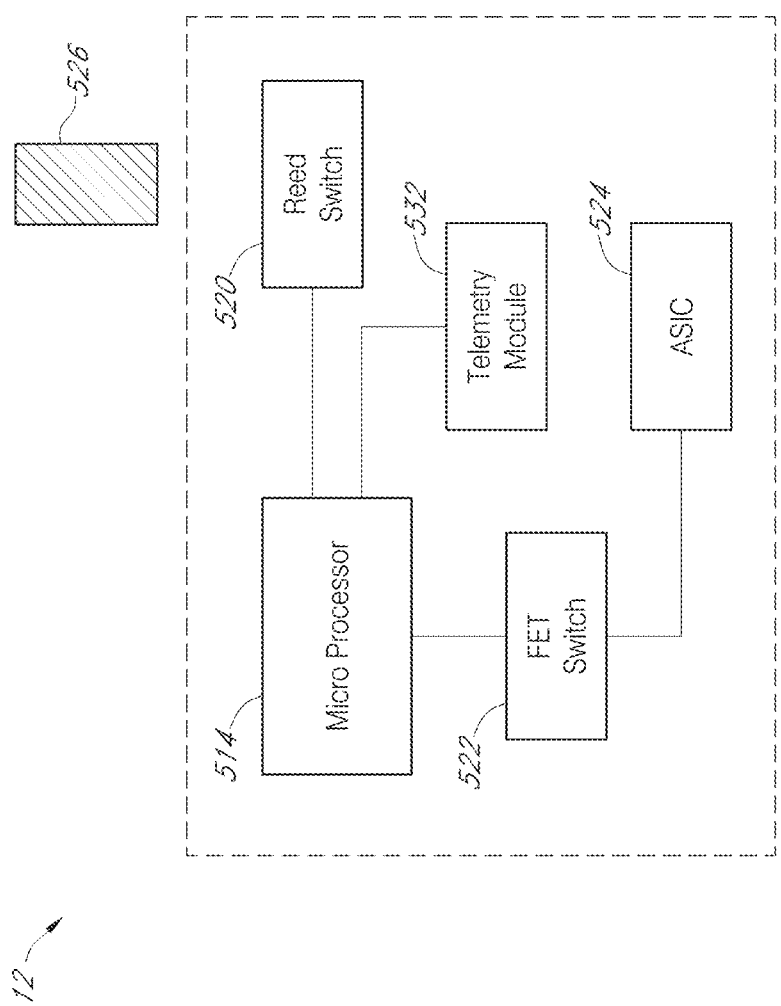
FIG. 5A is a simplified block diagram of an embodiment of sensor electronics module with a low power storage mode feature.

FIG. 5A is a simplified block diagram of an embodiment of sensor electronics module 500 with a low power storage mode feature. For ease of explanation, FIG. 5A only illustrates select components of a sensor electronics module 12 and it is understood that further components can be incorporated into sensor electronics module 12, such as any components discussed above with reference to FIG. 2A.

As illustrated in the embodiment of FIG. 5A, sensor electronics module 12 includes reed switch 520 configured to switch between a first state (e.g., closed state) when a magnetic force is applied to the reed switch and second state (e.g., open state) when the magnetic force is removed or sufficiently diminished. Reed switch 520 is operatively connected to system processor 514, which is in turn operatively connected to ASIC 524 via FET switch 522. Telemetry module 532 is also operatively connected to microprocessor 514.

An exemplary process 550 for placing sensor electronics module 12 into a storage mode and taking sensor electronics module 12 out of the storage mode will now be described with reference to the flowchart depicted in FIG. 5B. It is understood that process 550 is illustrative only, and that additional steps 550 can be added and/or one or more steps of process 550 can be removed. In addition, the steps of process 550 are not limited to the described order.

Process 550 starts with activating a storage mode at block 552. A variety of methods can be used to activate the storage mode. In some embodiments, a storage mode command is transmitted from an external telemetry device and received by sensor electronics module 12 via telemetry module 532. The telemetry module 532 relays the storage mode command to microprocessor 514, which, in response, initiates a storage mode routine. In some embodiments, a storage mode command can be initiated by inputting a command via a user interface, such as user interface 222 of FIG. 2, of a sensor electronics module 12.

Further to block 552, the storage mode routine can include turning off electronic components of sensor electronics module 12 and/or placing electronic components of sensor electronics module 12 in a low power mode (also referred to as a sleep mode). In one embodiment, microprocessor 514 is placed in a low power mode and all other electronic components that need not be used during storage of the sensor electronics module 12, such as a potentiostat 210, and any unneeded circuits are turned off. For example, processor 514 of FIG. 5A can send a switch enable signal via a data line to turn off FET switch 522, which, in turn, turns off ASIC 524.

Also included in block 552, magnet 526 is placed in proximity to reed switch 520 to cause reed switch to be in a first state (e.g., a closed state). In one embodiment, reed switch 520 needs to be in the first state prior to sensor electronics module 12 receiving the storage mode command in order for the storage mode routine to be initiated. In another embodiment, the storage mode interrupt routine is initiated as long as reed switch 520 is placed in the first state during a predetermined amount of time after the sensor electronics module 12 receives the storage mode command.

Next, at block 554, microprocessor 514, while in a low power mode, monitors for an interrupt signal from reed switch 526. In some embodiments, an interrupt signal is sent from reed switch 526 when switched to a second state (e.g., open state), which occurs when magnet 526 is no longer in sufficient proximity to reed switch 520 to keep reed switch in the first state. This can occur, for example, when sensor electronics module 12 is removed from storage packaging in which magnet 526 can be embedded.

At decision block 556, process 550 determines whether an interrupt signal has been received. If not, then process 550 returns to block 604 to continue monitoring for an interrupt signal. If it is determined that an interrupt signal has been received, then process 550 proceeds to block 558.

Process 550 initiates a state machine validation routine at block 558. In some embodiments, the state machine validation routine verifies at predetermined intervals that the reed switch signal continues for a predetermined amount of time. For example, each predetermined interval can be one minute and the predetermined amount of time can be five minutes. In such an example, processor 514 can be woken each interval (e.g., each minute) to verify that the reed switch signal continues to be in the inactive state and the processor is placed in a sleep mode in between verification intervals to conserve power. Should microprocessor 514 determine that the reed switch signal has returned to the activated state—which can occur if magnet 526 is moved to be in sufficient proximity to reed switch 520 or if a signal glitch occurs, (which can be further mitigated using a debounce or second check to make sure the signal was not glitched), for example—then the validation routine ends and it is determined that the removed magnet state is not valid. However, the removed magnet state is considered valid if, after the expiration of the predetermined amount of time, microprocessor 514 has seen the correct reed switch signal level at each verification interval.

Next, decision block 560 queries whether the removed magnet state is valid. If not valid, then process returns to block 604. However, if valid, then process proceeds to block 562.

At block 562, process 550 deactivates the storage mode. Here, components of sensor electronics module 12 are switched into a normal operation mode. For example, microprocessor can be woken out of a sleep mode and turn on FET switch, which, in turn, enables ASIC 524 and any other components of sensor electronics module 12 that are used during a normal operation mode.

In some embodiments, process 550 can be performed not only when the sensor electronics module 12 is placed in storage, but also after sensor electronics module 12 is initially removed from its packaging. In this way, a user can place the sensor electronics module in a low power mode whenever desired; for example, when on an airplane or any other time it is determined that the sensor electronics module 12 should not or need not be powered. In this regard, some embodiments provide a magnetic clip (not shown) that is configured to hold magnet 526 in proximity to reed switch 526. A user can then attach the magnetic clip to sensor electronics module 12 and initiate a storage mode command to begin process 550.

In some embodiments, sensor electronics module 12 can be configured to prevent re-entry of the storage mode once taken out of the storage mode. This may be beneficial to prevent the sensor electronics module 12 from accidentally re-entering storage mode during use, among other reasons. Sensor electronics module 12 can be configured to prevent storage mode after the sensor electronics module 12 is taken out of storage mode by disabling reed switch 520 or the data line connecting reed switch 520 to processor 514, for example.

In some embodiments, a process is used to prevent or reduce the likelihood of inadvertent reentry into storage mode. For example, in one implementation, a simple transition on the reed switch is not sufficient to put the transmitter back in storage mode. In one embodiment, a specific complex magnetic pulse waveform is required in order to put the sensor electronics module 12 into a test mode in which the sensor electronics module is configured to be able to receive a storage mode command over an RF interface. In addition, the storage mode command can be unique for each sensor electronics module 12 and can be required to be received within a predetermined amount of time (e.g., 10 seconds) of the sensor electronics module 12 successfully entering the test mode. If any of these conditions are not met, the sensor electronics module 12 does not return to storage mode.

In some embodiments, sensor electronics module 12 includes a light-sensitive sensor that takes the sensor electronics module out of a storage mode when the light-sensitive sensor is exposed to light. To illustrate, sensor electronics module 12 can be placed in a low power, storage mode during manufacture, shipment and storage so the sensor electronics module consumes little power. A light-sensitive sensor can be included in sensor electronics module 12 that is shielded from light by a protective cover and the sensor electronics module placed in a storage mode in a similar manner as described above. Thus, during manufacture, shipment and storage of sensor electronics module 12, the sensor electronics module can be in the storage mode.

A user can remove the protective cover—thereby exposing the light-sensitive sensor to light—to cause the sensor electronics module to switch from the storage mode to a higher power, operational mode (e.g. when the sensor electronics module 12 needs to be woken up for use).

Figure 6:
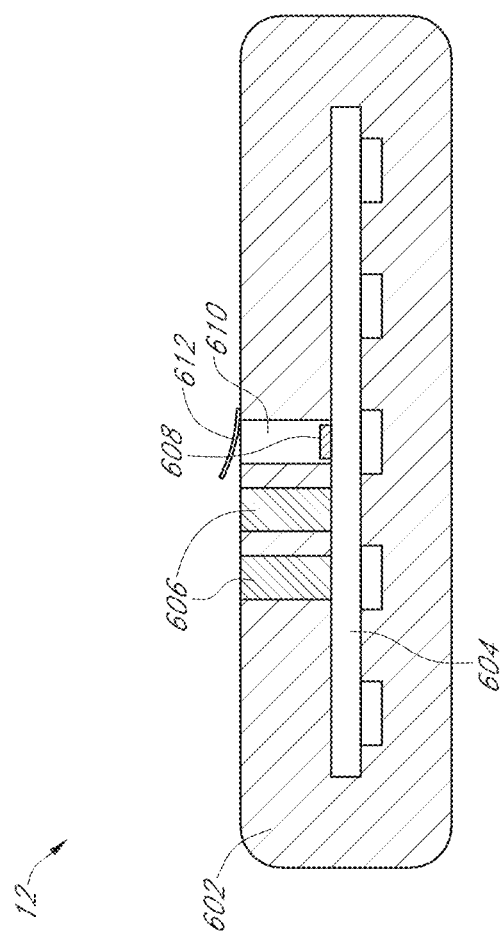
FIG. 6 is a cross-sectional view of sensor electronics module having a light-sensitive senor in accordance with one embodiment.

FIG. 6 is a cross-sectional view of sensor electronics module 12 having a light-sensitive senor in accordance with one embodiment. Here, sensor electronics module 12 includes housing 602 encasing printed circuit board (PCB) 604. PCB 604 includes electronic circuitry used for driving an analyte sensor, processing sensor output, transmitting sensor data and other functions of the sensor electronics module 12 described herein. Electrical contacts 606 configured to either directly or indirectly couple PCB 604 to analyte sensor 10, for example. Electrical contacts 606 can be metal wires that extend through housing 602 electrically coupled to PCB 604. In addition, a light-sensitive component 608 is disposed on and electrically coupled to PCB 604. Light guide 610 extends through housing 602 and over light-sensitive component 608 to allow light to propagate from outside of housing 602 onto light-sensitive component 608.

Light-sensitive component 608 can generate an electrical signal output by converting light energy (photons) into electricity (electrons). In one embodiment, light-sensitive component 608 measures frequencies limited to one or more of infrared, visible and ultraviolet light spectrums. The light-sensitive component 608 can comprise a photo-emissive cell, a photo-conductive cell, a photo-voltaic cell and/or a photo-junction device, for example.

Figure 5B:
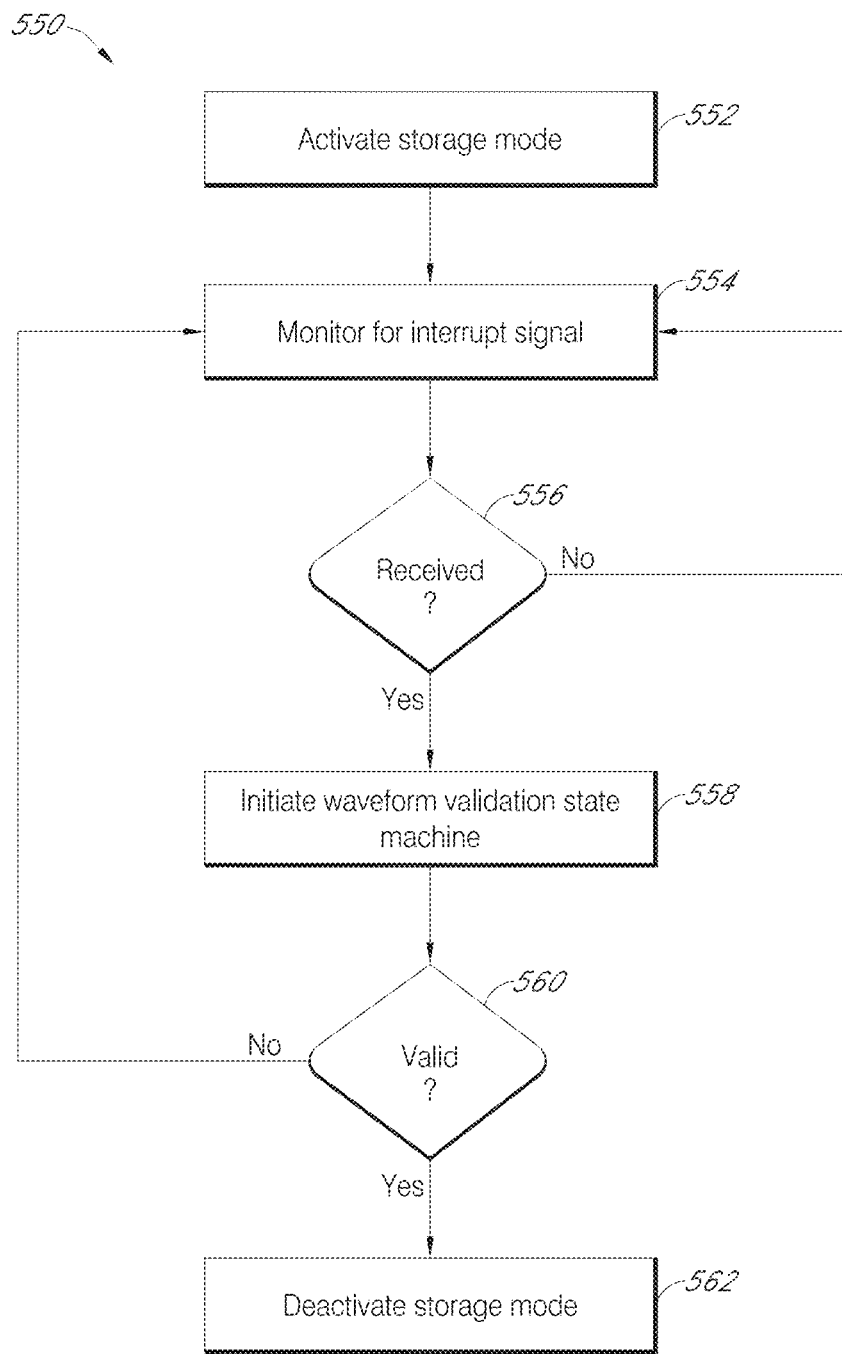
FIG. 5B is a flow chart of an exemplary process for placing sensor electronics module into a storage mode and taking sensor electronics module out of the storage mode.

In one embodiment, sensor electronics module 12 can be taken out of a storage mode in the same manner as described with respect to FIG. 5B, except light-sensitive component 608 initiates an interrupt signal instead of the reed switch described above.

Further, FIG. 6 illustrates a removable protective shield 612 that prevents exposure of light onto light sensitive component 608. Removable protective shield 612 can be an opaque, removable adhesive tab, for example. For ease of understanding, removable protective shield 612 is illustrated as being partially peeled off of electronics module 12 in FIG. 6.

The following is a manufacturing process which can be used to make sensor electronics module 12 of FIG. 6, in accordance with some embodiments. First, electrical contacts 606 (which can comprise metal wires), light sensitive component 608 and light guide 610 can be coupled to PCB 604 using any suitable, known coupling method. PCB 604—with the electrical contacts 606 light sensitive component 608 and light guide 610 coupled thereto—can then be placed in a mold shaped as the exterior housing of the sensor electronics module 12. An epoxy resin can then be cast into the mold and cured to form housing 602.

In one embodiment, electrical contacts 606 and light guide 610 are initially of sufficient length to extend beyond the epoxy in the mold. Once cured, however, the electrical contacts 606 and light guide 610 are machined flush with the outside of the sensor electronics module housing 602, leaving contacts 606 exposed on the surface of sensor electronics module 12, as well as an optical window to light sensitive component 608 formed by light guide 610.

The above-described manufacturing process can result in a water proof encapsulation of PCB 604, while leaving contacts 606 and light guide 610 exposed.

A sensor kit can also be provided that includes one or more sensor electronics modules 12 and a plurality of sensors 10. The number of sensor electronics modules 12 and sensors 10 included in the kit can be selected so that a user can use the components in the kit to monitor an analyte concentration continuously or near continuously for an extended period of time, such as 1 month, 6 months or a year. Accordingly, the sensor kit can include one or a plurality of sensor electronics modules 12 (e.g., 1, 2, 3 or more sensor electronics modules) and a plurality of sensors 10, such as 5, 7, 10, 15, 20, 50 or 100 sensors. A plurality of mounting units 240 can also be provided in the kit, and, instances in which the mounting unit is disposable with the sensor, the kit can provide each sensor held in a respective mounting unit. On the other hand, the kit can include fewer mounting kits than sensors in instances where a mounting unit can be reused with more than one sensor. One or more applicators configured to implant a sensor 10 into a host can also be provided in the kit, such as an applicator described in more detail in U.S. Pat. No. 7,310,544, entitled, "Methods and Systems For Inserting A Transcutaneous Analyte Sensor", issued on Dec. 18, 2007 and filed on Mar. 10, 2005, the content of which is incorporated herein by reference in its entirety.

Each sensor electronics module 12 can also be held in packaging in the kit. In some embodiments, the packaging can include a magnet that is held in sufficient proximity to each of the sensor electronics modules so as to keep the sensor electronics module in the storage mode while the sensor electronics module is in the packaging. Further, the packaging and magnet can be configured in a way so that removing the sensor electronics module from the packing causes the electronics module to switch from the storage mode into the normal operation mode. Various packaging configurations can be used to implement this feature.

In one embodiment, the packaging can comprise a storage bag and magnet attached to the bag. Each sensor electronics module 12 provided in the kit can be held in the bag. A user can then remove the sensor electronics module from the bag to cause the sensor electronics module to switch out of the storage mode and into the normal operation mode.

In one embodiment, the packaging can include a removable tab attached to the sensor electronics module. The tab can hold the magnet in sufficient proximity to the electronics module to keep the electronics module in the storage mode. A user can then remove the tab to cause the sensor electronics module to switch out of the storage mode and into the normal operation mode.

In one embodiment, the packaging can include a tray configured to hold one or more sensor electronics modules provided in the kit. For example, the tray can be plastic and formed to have a plurality of molds configured to hold components of the sensor system, including one or more sensor electronics modules. The tray can include a magnet located in proximity to each sensor electronics module held in the tray to keep the sensor electronics module in the storage mode. A user can then remove the sensor electronics module from the tray to cause the sensor electronics module to switch out of the storage mode and into the normal operation mode.

Accordingly, a sensor kit can be provided to a user with each of the sensor electronics modules 12 that are part of the kit in the storage mode. A user can then take a first sensor electronics module out of the kit (which switches the first sensor electronics module to normal operation mode) and use the first sensor electronics module with sensors provided in the kit until an occurrence of an event that triggers the need to use a new sensor electronics module. Once a new sensor electronics module is needed, the user can take a second sensor electronics module out of the kit (which switches the second sensor electronics module to normal operation mode) and use the second sensor electronics module with sensors provided in the kit until a new sensor electronics module is needed, and so on. In this manner, the useful life of sensor electronics modules can be extended because each sensor electronics module can be held in a low power storage mode until use (e.g., when the sensor electronics module is removed from its packaging).

As discussed above, a user may need to switch to a new sensor electronics module 12 upon the occurrence of an event. The event can be when the sensor electronics module's battery power is too low to continue using the sensor electronics module or the event can occur upon a detection of an error in the operation of the sensor electronics module. The event can also be triggered upon the expiration of a predetermined amount of time based on a length of time that the sensor electronics module is in the normal operation mode.

Further, a sensor kit can be used to allow for uninterrupted measurements. In some embodiments, when sensor 10 needs to be changed, a user detaches the sensor electronics module 12 from mounting unit 240, which holds sensor 10, and discards the mounting unit and sensor. The user then implants a new sensor using a new mounting unit, and attaches the sensor electronics 12 module to the mounting unit. Not only can it take time to implant the new sensor, but it can also take time for the new sensor to stabilize in the host before the new sensor provides reliable data.

Accordingly, in some embodiments, a sensor kit can provide two or more sensor electronics modules. Prior to a first sensor needing to be changed (e.g., because the sensor is approaching the end of its useful life), a user can implant a new, second sensor and attach a second sensor electronics module to the new sensor. The user can then wait for the new sensor to stabilize and calibrate prior to removing the first sensor and detaching the first sensor electronics, which was coupled to and obtaining readings from the first sensor. In some embodiments, a user can place the electronics module not currently being used (i.e. the first sensor electronics module) in a storage mode by, for example, initiating a storage mode routine and placing the first sensor electronics module back into the packaging to maintain storage mode until the first sensor electronics module is once again used.

Thus, having two or more sensor electronics modules in a sensor kit can provide several benefits. First, the user can obtain uninterrupted measurements, without any downtime between switching sensors. Second, the first electronics module can be configured to calibrate the second electronics module. This calibration can be performed while both sensor electronics modules are obtaining measurements in a host at same time. In this manner, the second sensor can be calibrated, at least in part, on data generated by the first sensor (which was already calibrated) while both the first and second sensors are concurrently implanted in the host. Using a first electronics module to calibrate a second electronics module is discussed in more detail in U.S. Patent Publication No. US-2006-0258929-A1, the content of which is incorporated by reference herein in its entirety. Another benefit is that the first sensor and first electronics module can continue to provide measurements in the event it is determined that the second sensor or second electronics module is faulty during the time period both sensors are being used.

Transmitter Interrupt Glitch Filter

Some embodiments also include an interrupt glitch filter that determines whether a waveform signal is valid. An interrupt glitch filter can be used in electronics module 12 or 12, for example. The interrupt signal can be the waveform signal configured to wake the electronics module 12 from a storage mode, as discussed with reference to FIGS. 5 and 6, or can be any other waveform signal used during operation of sensor electronics module 12 or 12 to cause processor 214 or 514 or other sensor electronic components to switch between different states of operation, such as between a low power state of operation (e.g., sleep mode) and powered up state of operation or other routine.

An interrupt glitch signal, on the other hand, can be a transient signal inadvertently generated due to vibration of the sensor electronics module or to other spurious causes. An interrupt glitch signal can cause false and inadvertent interrupts, which can place sensor electronics module into an unusable state unless the sensor electronics module is, for example, reset.

In some embodiments, a waveform signal comprises a relatively complex waveform so a valid waveform signal can be discerned from a single signal glitch. The complex waveform can be designed so that it is highly unlikely that a single signal glitch would be the same as a valid waveform signal.

Further, in some embodiments, a processor of the sensor electronics module wakes from a sleep state and enters an operational state to determine whether a received interrupt signal is valid. If not valid, the processor returns to a sleep state. Entering the operational state can consume a significant amount of power, however. For example, entering the operational state may power up numerous clocks, etc. that consume power. Thus, entering the operational state each time an interrupt signal is received can consume a lot of power if numerous interrupt glitches are received.

In some embodiments, the processor or other logic separates an interrupt filter routine from normal operation so that the processor need not wake to the operational state until the filter logic determines whether or not a signal is a valid interrupt signal. Instead, the processor or other electronic components enter an interrupt check routine state, which can consume less power than waking the processor to its operational state.

In one embodiment, an interrupt filter routine can execute logic, which can be implemented in the form of a state machine, configured to decipher whether an interrupt signal is part of a valid waveform signal or whether it is an inadvertent glitch. If the filter routine logic determines the entire waveform signal is valid, then—and only then—is the core processor of the sensor electronics module allowed to discontinue its current mode of operation (e.g., exit a low power mode).

In one exemplary implementation, interrupt logic, separate from a core electronic module processor, tests the set of signals to determine whether a waveform signal is valid. The logic can comprise a software routine that is separate from the software used by the processor during normal operation. As discussed above, a valid waveform signal can be designed as a complex waveform. Upon receipt of each signal, the interrupt logic iteratively tests sections of the waveform to determine whether each section is valid. That is, the interrupt logic tests a first section of the waveform to confirm that the first section is the same as a first section of a valid waveform signal, followed by a second section, and so on, until the entire waveform is analyzed. If, however, any section is determined to be different from a valid waveform, then the interrupt routine determines that the single signal is not valid (i.e. an interrupt glitch), stops analyzing any further sections of the waveform and resets the state machine. If, on the other hand, the entire waveform is tested and each section is determined to be valid, then the interrupt routine determines that the waveform signal is valid and initiates a system wake up routine.

In one embodiment, a state machine performs a plurality of iterative tests (such as 2, 5, 10, 20 or more) on each individual signal to determine if the entire waveform of the signal follows a valid predefined waveform. If, after the completion of any one of the plurality of tests, the state machine determines that the waveform is not valid, then the state machine resets and the state machine waits for the next individual signal. In this manner, the state machine need not analyze a complete waveform signal to determine whether or not it is faulty. An iterative approach, such as the approach discussed above, can save power by quickly determining if a waveform signal is faulty and ending the process should one of the earlier sections being tested confirm that the signal is faulty—as opposed to analyzing the entire waveform regardless of whether earlier sections of the waveform are faulty.

Automatically Switching on Sensor Electronics

With reference to FIG. 1, some embodiments of a system for continuous measurement of an analyte automatically switch a sensor electronics module 12 from a low power mode (e.g., power off mode or low power storage mode) to a higher power operational mode when the sensor electronics module is attached to a disposable sensor, such as continuous analyte sensor 10 and/or mounting unit 240. Doing so can reduce power consumption during the shelf-life of the sensor electronics module 12 as well as in between sensor attachments. As described above with respect to FIGS. 2B and 2C, some embodiments of sensor system 8 can use sensor electronics module 12 that is configured to be releasably attached to mounting unit 240, wherein the mounting unit holds sensor 10 when the sensor is implanted in a host.

In some embodiments, a connector pad of sensor electronics module 12, configured to contact corresponding contact(s) of mounting unit 240, can be split into two individual, electrically insulated connectors. The contact(s) of the mounting unit 240 can be in the form of a conductive, flexible "puck", designed to make contact with the corresponding "split" connector of the sensor electronics module when sensor electronics module is attached to the mounting unit. Once in contact, the split connector and the conductive puck result in a short circuit. This can cause sensor electronics module to switch on after an impedance measurement or switch on a battery voltage to wake up the sensor electronics module.

Figure 8:
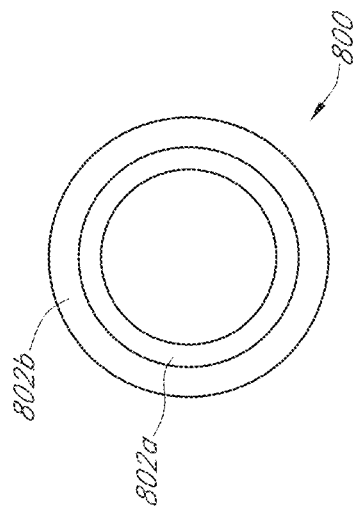
FIG. 8 illustrates an embodiment of a split connector having a concentric layout in accordance with one embodiment.
Figure 7:
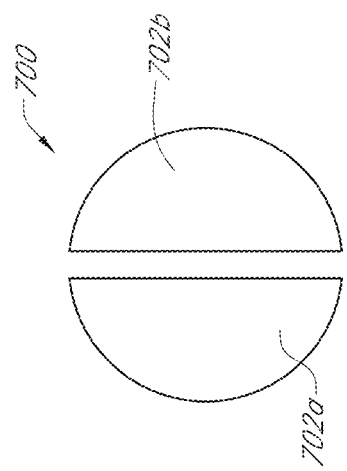
FIG. 7 illustrates an embodiment of a split connector having an axial symmetric layout in accordance with one embodiment.

FIGS. 7 and 8 are top views of respective embodiments of split connectors 700, 800 of sensor electronics module 12. FIG. 7 illustrates an embodiment of a split connector 700 having an axial symmetric layout, where connector 700 is split into two semicircular partial contacts 702a and 702b. FIG. 8 is an embodiment of a split connector 800 having a concentric (co-axial) design, where a first partial contact 802a is encircled by a second partial contact 802b. A space is provided between contacts 802a and 802b to insulate the contacts from one another.

Figure 9:
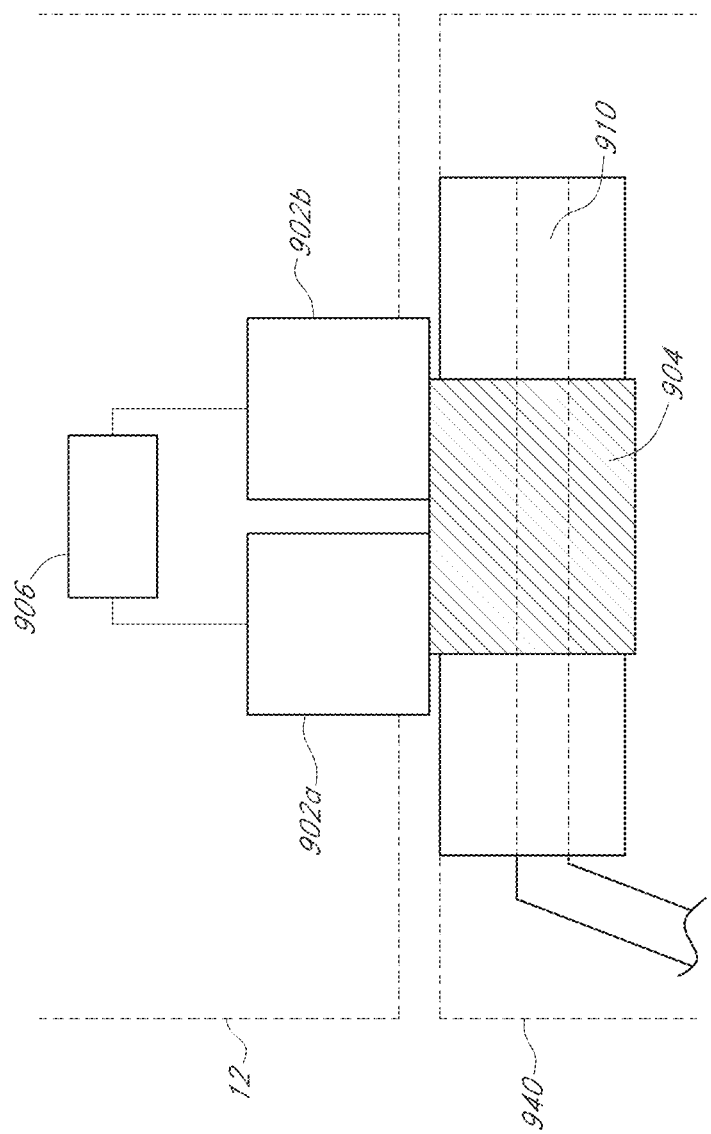
FIG. 9 is a schematic cross-sectional view of a sensor electronics module attached to a mounting unit in accordance with one embodiment.

FIG. 9 illustrates a partial cross-sectional view of a sensor electronics module attached to a mounting unit in accordance with one embodiment. Here, sensor electronics module 12, is attached to mounting base 940, which can include any of the features of mounting base 240 described herein. When attached, both partial contacts 902a and 902b of sensor electronics module 12 make contact with conductive sensor puck 904 of mounting unit 940. Partial contacts 902a and 902b can be partial contacts 702a and 702b, respectively, or partial contacts 802a and 802b, respectively, discussed above. The contact allows for switching on sensor electronics module 12 as well as providing connection of a potentiostat (not shown in FIG. 9) in the sensor electronics module with sensor 910.

The embodiment of FIG. 9 uses electronic switch 906 based on a measurement of impedance (resistance) between contacts 902a and 902b. Without sensor puck 904 in contact with partial contacts 902a and 902b, the impedance measurement should be, theoretically, infinitely high. When sensor electronics module 12 is attached to sensor unit 920, conductive puck 904 shorts the two contacts 902a and 902b, which results in a measurable, low resistance. This resistance can be measured by a simple circuit incorporated in switch 906. The circuit can draw minimum or no power. Upon measuring the low resistance, switch 906 can switch power up the electronics module 12 from a low power state.

The switch 906 can connect and disconnect a battery circuit to cause sensor electronics module 12 to switch between a low power state and a high power state. The battery circuit can be separate from or incorporated in the sensor electronics module 12. Further, when connected, the battery circuit can power some or all the components of the sensor electronics module in some embodiments. For example, in some embodiments a first battery circuit connected to the switch 906 provides power to some, but not all, components of the sensor electronics module, such as components used to drive the sensor during a measurement cycle, when connected, and a separate, second battery circuit provides power to components of the sensor electronics module regardless of whether the first battery circuit is connected via the switch. The first and second battery circuits can be powered by the same or different batteries.

When switch 906 is connected to a battery circuit, connection of the mounting base 940 to sensor electronics module 12 causes switch 906 to close the battery circuit, which powers up the sensor electronics module. Further, disconnecting the sensor unit 920 from the sensor electronics module 12 causes switch to open the battery circuit, which powers down the sensor electronics module.

Sensor Electronics Module with Improved Shelf Life and Use Life

In some embodiments, a sensor electronics module, such as sensor electronics module 12, is continuously powered on from the time batteries are permanently attached during manufacturing. Being continuously powered can give the sensor electronics module 12 a short usable life, which can include the time it is stored on a shelf and the time of its normal use. It is desirable to increase the shelf-life of sensor electronics module 12, as well as develop new designs with smaller batteries and/or more features that use additional power, yet do not shorten the sensor control module's usable life.

The sensor electronics module 12 can be configured to be permanently switched on just prior to shipment by a manufacturer or distributor, for example, so that the sensor electronics module 12 does not consume power while sitting in storage at the manufacture or distributor. In one embodiment, an external switch is mounted on a housing of the sensor electronics module 12 to turn on the sensor electronics module.

The sensor electronics module 12 can also be configured to turn off or enter a low power mode when not in use, thereby extending the useful life of the sensor electronics—particularly if there are long periods of non-use between sensors.

Some embodiments are configured to power on the sensor electronics module 12 (e.g., cause the sensor electronics module to enter a higher power consuming, operational mode) only when a sensor reading above a predetermined threshold is detected. This feature can be particularly advantageous in embodiments where a substantial amount of total power consumption by the sensor electronics module 12 is due to wireless transmission and/or receipt of data; as opposed to a sensor measurement, which can consume much less power in some embodiments. Accordingly, the sensor electronics module 12 can be configured to be in a low power mode, wherein the sensor electronics module periodically performs measurements. During the low power mode many of the other features of the module 12 that are not needed to perform the measurements can be turned off, such as telemetry module 232. In one embodiment, if the sensor electronics module 12 measures below a predetermined threshold, then sensor electronics module remains in a low power mode. Should the threshold be exceeded, then the sensor electronics module 12 can enter an operational mode. The threshold can be selected based on values that would indicate the sensor electronics module 12 is not operatively connected to sensor 10 or, even if connected to the sensor, the sensor is not implanted in a host. The threshold can be zero measured counts, zero measured current or zero measured response. The threshold can also be set to be slightly above zero so that noise, leakage current or the like does not falsely indicate that the sensor electronics module 12 is operatively connected to sensor 10.

Some embodiments of the sensor electronics module 12 continuously or near continuously sample and filter raw data, which can consume a significant amount of battery power. However, in other embodiments, while in a low power mode, the sensor electronics module 12 can be configured to sample less frequently (e.g. a measurement each hour) to further conserve power. Doing so can be particularly beneficial for embodiments of the sensor electronics module 12 that use a significant amount of power when performing a measurement.

In some embodiments, the sensor electronics module 12 is configured to automatically enter a low power mode if the sensor electronics module is operatively connected to the same sensor for longer than a predetermined amount of time. A sensor can have a known useful life, after which the sensor may provide unreliable readings. Thus, the sensor electronics module 12 can be configured to enter a low power mode after a sensor has been used for a predetermined amount of time to prevent further use of the sensor, and indicate to the user that the sensor needs to be replaced with a new sensor. Once a user attaches a new sensor, then the sensor electronics module 12 can return to normal operating mode.

In some embodiments, a wireless signal can be sent from a display device 14, 16, 18 or 20 (FIG. 1) or other transmitter to the sensor electronics module 12 to turn on the sensor electronics module or to cause the sensor electronics module to enter an operational mode. The signal can be initiated by an end-user at the start of use of the system or by a manufacturer or distributor just prior to shipping. This feature can be beneficial because listening for a signal can use less power than transmitting.

The sensor electronics module 12 can also have contacts located on its housing. In one embodiment, the contacts are configured to contact a conductive area on mounting unit 240. Upon connection of the contacts with the conductive area, the sensor electronics module 12 is configured to switch from a low or no power mode to an operational or higher power mode.

Referring back to FIG. 2C, contact sub-assembly 246 of mounting unit 240 can have contacts that contact corresponding contacts of sensor electronics module 12 when the electronics unit is attached to the mounting unit. In some embodiments, the contacts (not shown) of the sensor electronics module 12 can function as a mechanical switch for switching on the sensor electronics module. In this regard, the contacts can translate within the sensor electronics module 12 such that when the sensor electronics module is coupled to the mounting unit 240, the contacts of sensor subassembly 246 cause the contacts of the sensor control unit to move. This movement can trigger a switch (not shown) in the sensor electronics module, causing the sensor electronics module to enter a new mode of operation (e.g. switch from a low power mode to a higher power operational mode). The switch can either directly supply power components of the sensor electronics module 12 or can function as a sensor that initiates a routine that causes the sensor electronics module to enter a different mode of operation. In one embodiment, the contacts of the sensor electronics module 12 are attached to a PCB board that is configured to move when the contacts contact corresponding contacts of the mounting unit.

In some embodiments, the sensor electronics module 12 can include an accelerometer configured to detect a shake or tap scenario that causes the sensor electronics module to switch to a different operational mode. Thus, a user can switch the sensor electronics 12 module from a low power, standby mode to an operational mode by shaking the sensor electronics module in a predetermined way.

Method to Limit Re-Use of Sensor

Some embodiments can limit the re-use of a sensor. As discussed above, a sensor may have a defined period of time in which it can be used. After the expiration of the time period, some factors may dictate that the sensor should no longer be used, such as readings from the sensor no longer being accurate or sufficiently reliable, sensor degradation, or the like. In some embodiments, a sensor may be intended or approved for use for only 5, 7, 10 or 20 days after it is first implanted in a host. Thus, some embodiments employ systems and methods to prevent use or re-use of a sensor after a predefined period of use.

In some embodiments, battery power associated with a sensor is quickly used up or turned off upon the expiration of a predefined intended time-of-use period. For example, one embodiment powers the sensor 10 and/or sensor electronics module 12 using a disposable battery located in the mounting unit 240. At a programmed time (e.g., after the expiration of an intended use time period), electronics located in the mounting unit 240 or sensor electronics module 12 can be programmed, or otherwise electronically configured, to rapidly consume the remaining power in the battery (e.g., at a significantly higher rate than during normal operation). Once consumed, the sensor 10 and associated mounting unit 240 is rendered unusable in the future because no battery power or insufficient battery power is provided to the sensor electronics module 12. A new sensor and mounting unit—which also contains a new battery—will then be needed to further operate the continuous analyte monitoring system. This configuration can prevent the sensor from being used beyond its intended use period, thereby reducing or eliminating inaccurate sensor readings due to a sensor being used beyond its intended use period.

Sensor Stabilization

Some embodiments also include pre-treating sensor 10 to stabilize the sensor prior to implanting the sensor or powering up one or more components of the continuous analyte monitoring system.

In some embodiments, an overpotential is applied to a sensor after sensor implantation. Applying the overpotential can bring the sensor to electrochemical equilibrium more quickly. In one embodiment, a predetermined amount of time is allowed to transpire before applying the overpotential to the sensor to reduce problems at sensor startup, such as inconsistent sensor run-in performance. The delay can vary depending upon the characteristics of the sensor and the bodily characteristics of the host. The delay in applying the overpotential after sensor implantation can be, for example, in a range of 1 min. to 12 hrs., including 1 min., 10 min., 1 hr., 2 hrs., 3 hrs., 5 hrs., and 12 hrs. In one embodiment, a clock starting the delay is triggered upon a detection of an event. The event can be sensor implantation into the host, connecting a sensor electronics module to the sensor, or a user input received by the sensor system, such as a user pressing a button on a sensor electronics module or display unit.

In some embodiments, to measure glucose concentration, a fixed voltage (e.g. 0.6V) can be applied between a working electrode and a reference electrode. The current generated can be proportional to the glucose concentration. If the bias potential on the working electrode is within the potential window for the glucose measurement, a small fluctuation in the reference electrode potential should not affect the measurement result. However, glucose measurement results can be affected if the reference electrode potential is varied significantly, thus shifting the bias potential on the working electrode outside the potential window.

The potential of a silver chloride (Ag/AgCl) reference electrode can be controlled by the Cl⁻ concentration near the electrode surface. If the Cl⁻ concentration near the electrode surface varies too much, the glucose measurement could be affected. If the voltage drop between the reference electrode and the working electrode varies too much, the glucose measurement can also be affected.

In some embodiments, inconsistent sensor performance at startup can be due to a change of Cl⁻ concentration near the Ag/AgCl surface or a change of voltage drop between the working and reference electrodes. After sensor insertion, as the membrane progressively hydrates, the Cl⁻ concentration near the Ag/AgCl electrode surface can change gradually. It can reach equilibrium state eventually, thereby stabilizing the Ag/AgCl reference electrode. When the membrane is hydrated, the voltage drop between the reference and working electrodes can be reduced. Therefore, some embodiments allow for sensor hydration prior to applying a bias potential to the senor or allow for sensor hydration by applying only a low bias potential to the sensor prior to applying a higher bias potential.

Further, some embodiments account for sensor run-in after initial implantation into a host to stabilize and equilibrate to the host's body before the sensor can provide sufficiently accurate measurements. It has been recognized that applying a potential to the sensor electrode(s) prior to sufficient run-in (e.g., because the sensor membranes are not yet fully hydrated) can alter or damage the electrode(s) or sensor membrane(s) such that start-up time and analyte sensitivity could be variable and difficult to predict. The sensor run-in period can vary depending upon the type of sensor and bodily characteristics of the host, and can last in the range of a few minutes to twelve hours or even longer, as non-limiting examples.

In some embodiments, a sensor is allowed to stabilize and equilibrate with the host's body before the sensor electronics module 12 is coupled to the sensor 10. This can allow appropriate hydration of the sensor membrane prior to applying a potential to the sensor electrode(s). In one embodiment, electronics in the sensor electronics module 12 and/or mounting unit 240 can be configured to have a programmed delay in which to normalize a time between sensor insertion and application of a potential across the electrode(s). The delay can be programmed into software, firmware or hardware, for example, and, in one embodiment, can be in the range of 1 to 30 minutes.

Use of such a delay between sensor implantation and applying a potential to the sensor electrodes can normalize the change in sensor sensitivity to analytes over time and aid in predicting sensor drift. Such a delay can also improve sensor accuracy, improve consistency from one sensor to the next, allow for a more precise prediction algorithm and reduce the need of reference measurements (e.g. finger stick glucose measurements) to account for changes in the sensor. In addition, when using a dual electrode configuration, where one electrode has an enzyme layer and the other electrode does not, a programmed time delay can improve consistency of the baseline between the enzyme and non-enzyme electrodes.

Additionally, some embodiments can eliminate or reduce run-in time and sensor drift problems by stabilizing the sensor (e.g., the sensor's membrane) prior to inserting the sensor in a host by soaking the sensor in a solution containing chemical stabilizers selected to stabilize the membrane the sensor during fabrication. The chemical stabilizers can stabilize the sensor membrane, even when being dried and stored for packaging, to remain in a state similar to that during use (i.e. when the sensor is implanted in a host and measuring an analyte concentration). In one embodiment, the sensor is allowed to run-in to a stable signal level and is then soaked in the chemical stabilizer during fabrication to maintain the membrane and the electrode in a stable configuration during storage. This can reduce the time required for a sensor to achieve a stable in-vivo signal. Exemplary chemicals that can be used to stabilize the sensor include, but are not limited to, polysaccharides and substituted derivatives, BSA, gelatin, lipids, polymers with free hydroxyl groups (PEG, others) and salts.

The following is an overpotential process in accordance with some embodiments. First, a glucose sensor is hydrated at open circuit or low bias potential (e.g., less than the operational bias potential, such as less than 600 mV) for a period of time ranging from about 0 min to 24 hours, for example 2, 4, 5, 10, or 20 minutes. Hydration can be accomplished in a calibrant, blood sample, host's blood or host's interstitial fluid, for example. Once hydrated, an overpotential is then applied in a range of about 600-1000 mV (e.g., 700, 800, or 900 mV) for a period of time ranging from about 0 min. to 60 min. (e.g., 1, 2, 5 or 20 minutes). After the overpotential period of time expires, the sensor can be placed in normal operation (e.g. at a 600 mV bias).

The following experiment is one example of applying an overpotential process in accordance with some embodiments. In this experiment, 15 intravenous continuous blood glucose sensors were used as control and 15 were tested with an overpotential process. The intravenous continuous glucose sensors and monitoring system used in this experiment is commercially available from Edwards Lifesciences located in Irvine, Calif. Both the control group and overpotential group used sheep blood having 100 mg/dL glucose concentration.

For the first 5 minutes, both the control group and overpotential group were hydrated in a calibrant and a bias potential was applied at 600 mV. After the hydration period, the bias potential was switched to 800 mV bias for the overpotential group. The control group was maintained at 600 mV. After five minutes at the 800 mV potential, the overpotential group was switched back to 600 mV. Both the overpotential group and control group were maintained at 600 mV throughout normal use of the sensor, wherein the system alternated between blood draw and calibrant flush cycles. The blood draw was a 5 minute cycle and the calibrant flush cycle was a 2.5 minute cycle.

Figure 19:
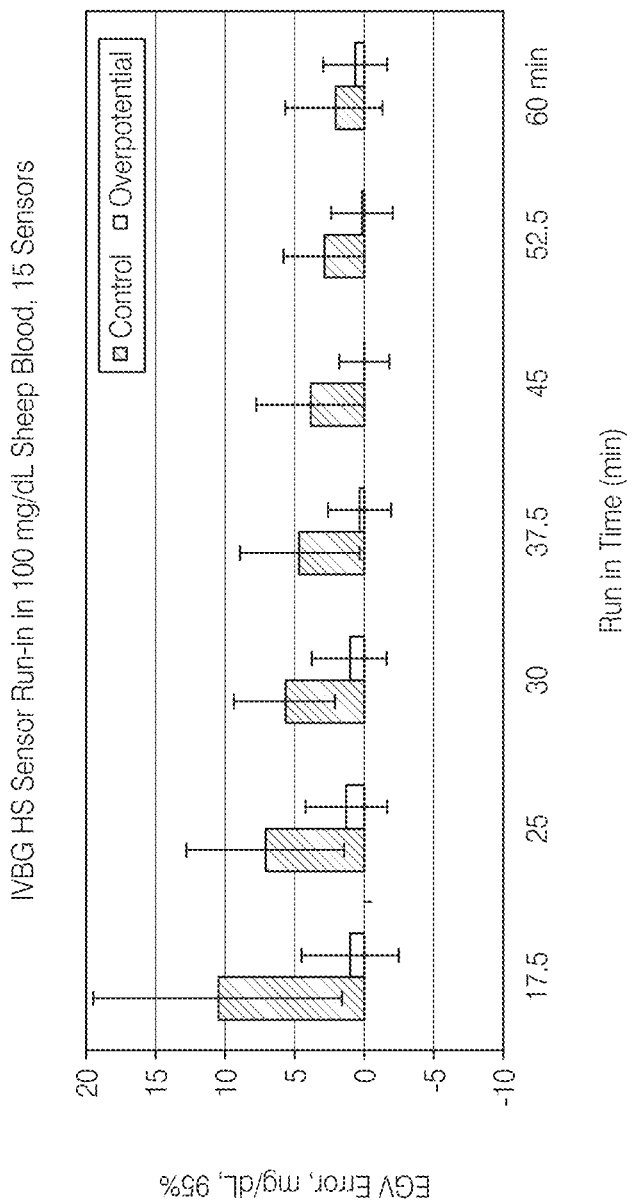
FIG. 19 is a graph of experimental results of applying an overpotential to a sensor system to improve sensor stabilization.

The results of the experiment are depicted in FIG. 19. As illustrated, the run-in time of the sensors in the overpotential group was significantly reduced. For example, the error of the sensors in overpotential group was found to be less at 17.5 minutes than the error in the control group at the 60 minute mark. Note that 17.5 minutes was the first reading in this experiment because the first reading was generated after applying the 5 minute hydration period, 5 minutes of control group at 800 mV, 2.5 minute calibrant flush cycle and 5 minute blood draw cycle.

External Electrode

Some embodiments utilize a three-electrode measurement cell, while others can utilize a two-electrode measurement cell. The three-electrode measurement cell can use a reference, working and counter electrode; whereas the two-electrode measurement can have a reference electrode and a working electrode only.

In a two-electrode measurement cell, the reference electrode can carry current, which, in some embodiments, consumes silver chloride (AgCl) disposed on the electrode. To accommodate a desired sensor life, enough silver chloride should be provided on the implanted sensor to account for the silver chloride consumption.

In the three-electrode configuration, when connected to the appropriate circuitry, the reference electrode can be made non-current carrying by guiding measurement current through the counter electrode instead. A counter electrode can be made of any suitable conductor, such as platinum or carbon.

Figure 10A:
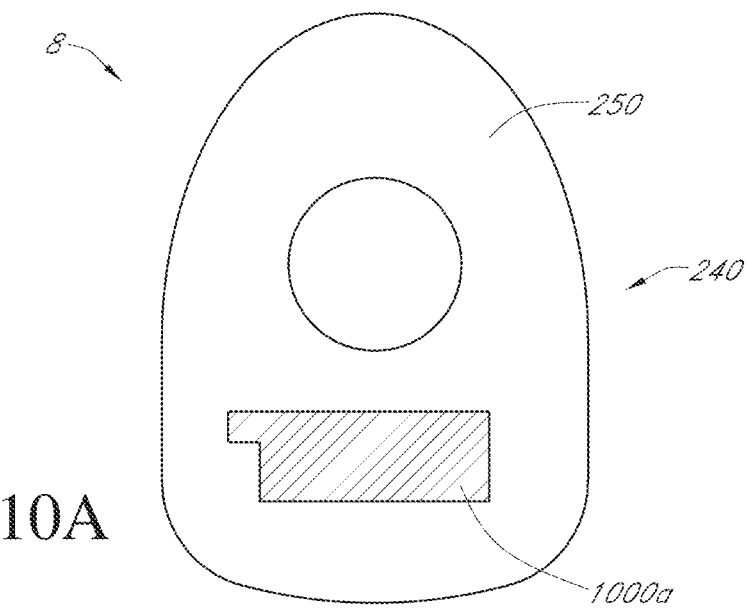
FIGS. 10A and 10B are respective bottom and cross-sectional views of a system having an electrode disposed on an adhesive patch in accordance with one embodiment.
Figure 10B:
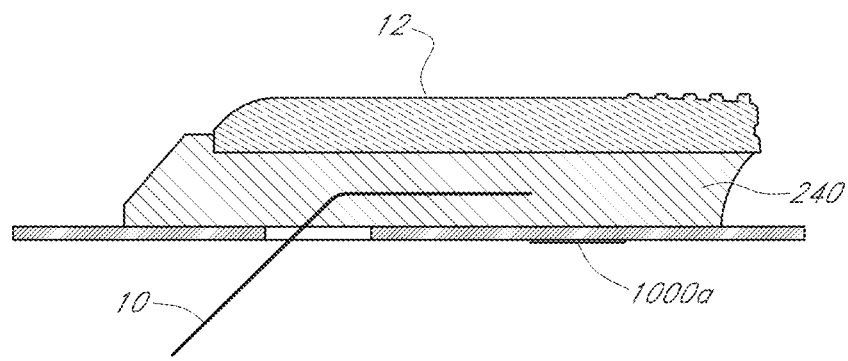

FIGS. 10A and 10B illustrate an embodiment of sensor system 8, including sensor electronics module 212 and sensor 210. Here, the sensor 10 is a three-electrode sensor configuration with counter electrode 1000a provided on an underside of an adhesive pad 250 of mounting unit 240. A screen printing process can be used to dispose the counter electrode 1000a on the adhesive pad 250, for example. The screen printing inks can include any suitable eclectically conductive material, such as platinum, carbon, gold, silver, silver chloride, an electrically conductive polymer or combinations thereof.

By providing an external counter electrode like counter electrode 1000a, the design constraints for a reference electrode are reduced, as the silver chloride of the reference electrode need not be consumed, but, instead, need only be used to provide a stable potential. As a result, the reference electrode can be made smaller, which can reduce the overall size or gauge of sensor 210. The reference electrode can be made smaller, for instance, by reducing the thickness of a silver chloride coating of the reference electrode and/or reducing the length of the sensor that is inserted into the host during use. Reducing the thickness or length can reduce the invasiveness of the sensor as well as improve the patient comfort of wearing the sensor.

Figure 10C:
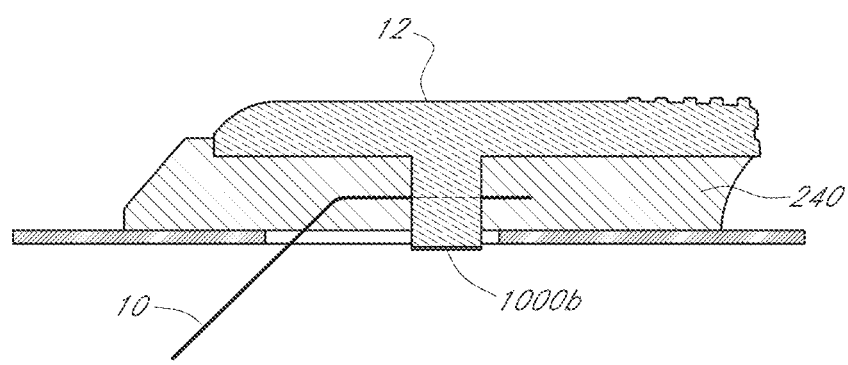
FIG. 10C is a cross-sectional view of a sensor system having a skin contacting electrode extending from a sensor electronics module and through a mounting unit in accordance with one embodiment.

FIG. 10C illustrates another embodiment, in which counter electrode 1000b is located on a skin contacting portion of the sensor electronics module 12. This embodiment maintains the benefits of the prior embodiment of FIG. 10B, but, in addition, removes the need to electrically contact a counter electrode on an adhesive pad with the sensor electronics module 12. Also, the counter electrode 1000b can be re-used along with the rest of the sensor electronics module 12, potentially resulting in less added cost. The counter electrode 1000b can be a layer of non-oxidizing metal, such as platinum, gold, or even stainless or surgical steel.

In the embodiments illustrated in FIGS. 10A, 10B and OC, counter electrode 1000 is configured to contact a host's skin, but not be transcutaneously positioned in the host. However, other embodiments can be configured to have the counter electrode transcutaneously positioned in a host by having the counter electrode comprise a needle or a plurality of micro-needles, for example, that can be at least partially implanted into a host.

In addition, counter electrode 1000 can be coated with a layer of a gel containing conductive ions. For example, the gel can be a hydrogel (e.g. poly-ethylene-glycol, poly-ethylene-oxide, poly-vinyl-pyrrolidone, poly-acrylamide etc.) containing salts such as sodium-chloride or potassium-chloride, and/or pH buffering components such as phosphoric acid. Coating the counter electrode with such a gel can improve the passage of current through the counter electrode into the skin.

In other embodiments, an external skin contacting reference electrode can be used on an under layer of the adhesive patch or skin contacting portion of sensor electronics module 12, similar to the external electrodes described above with reference to FIG. 10A-10C. Although not wishing to be bound by theory, it is believed that a stable potential need to be provided for a reference electrode, in contrast to a pathway for current in the case of a counter electrode. Thus, some embodiments can provide a stable potential by using a silver/silver-chloride (Ag/AgCl) electrode that is coated with a hydrogel layer. The hydrogel layer can contain needed chloride ions for a stable reference electrode and may be placed between the Ag/Cl electrode and skin of the host.

By providing an external reference, the dimensions (diameter and length) of the implanted portion of sensor 10 can be reduced, decreasing invasiveness and increasing comfort. The reference electrode can be used either in a 2-electrode system (e.g. where the measurement current travels through the reference) or in a 3-electrode system (e.g. where the current goes through a 3rd electrode, the counter electrode). In the latter case, the counter electrode can also be an external and skin-contacting electrode as described above with reference to FIG. 10A-10C.

Battery Replacement Device

Some embodiments include a replaceable battery in a housing of the sensor electronics module 12. To keep the size of sensor electronics module 12 small, it is often times desirable to use a small-sized battery that is replaceable. However, it can be difficult to replace a small-sized battery, especially by users with reduced vision and dexterity.

Figure 11A:
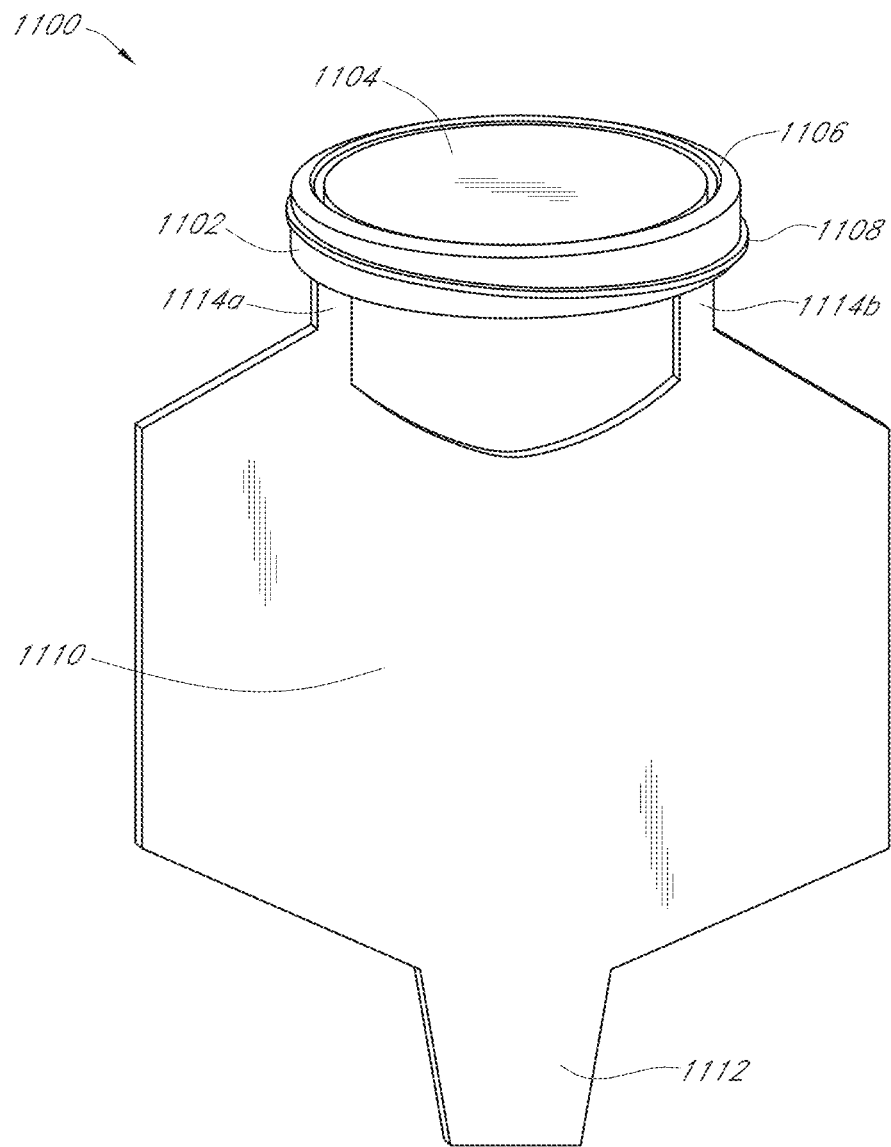
FIGS. 11A and 11B illustrates upper perspective and lower perspective views, respectively, of an embodiment of a battery replacement device that enables a user to easily replace a battery contained in sensor electronics module.
Figure 11B:
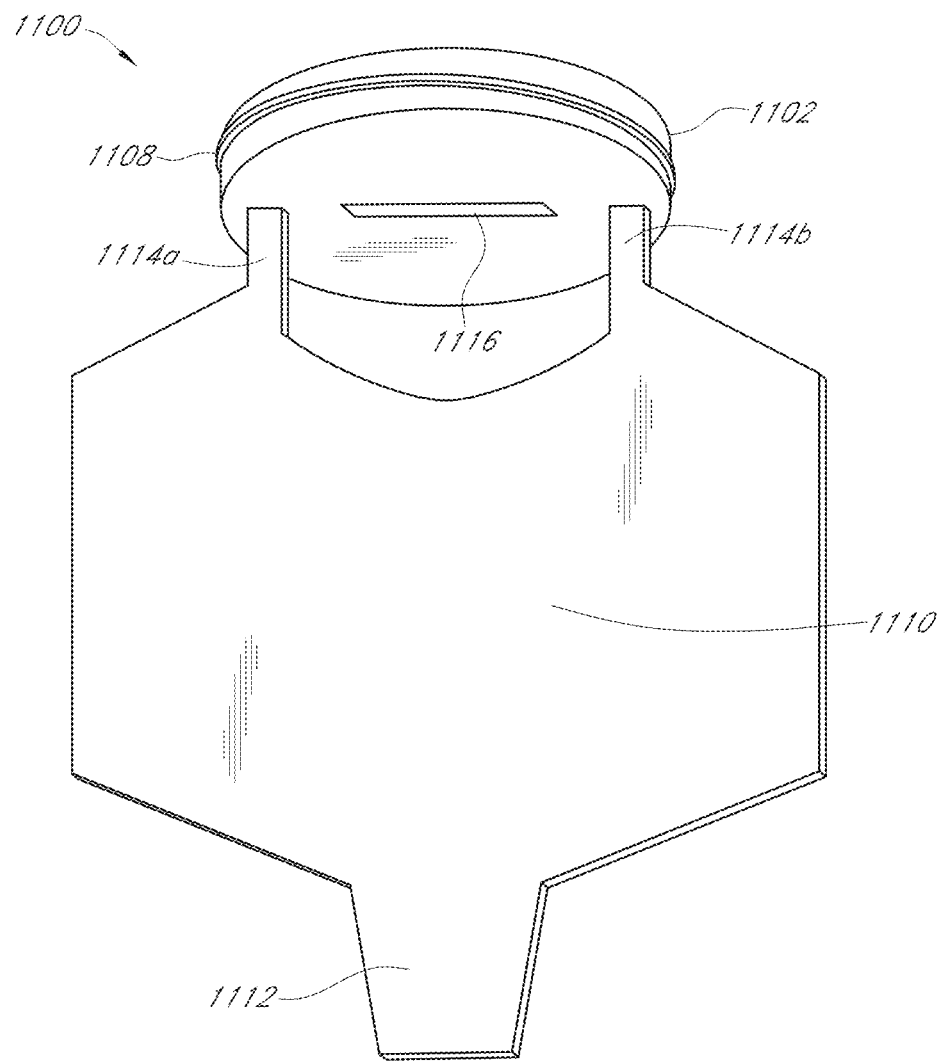

FIGS. 11A and 11B illustrates upper perspective and lower perspective views, respectively, of an embodiment of a battery replacement device 1100 that enables a user to easily replace a battery of sensor electronics module 12. As illustrated in FIGS. 11A and 11B, the battery replacement device 1100 includes a holder 1102 configured to hold a battery 1104. In one implementation, the holder 1102 can include a cup-shaped portion configured to hold the battery within a cavity of the cup, as is illustrated. Threads 1108 can be provided on the outside of the holder 1102. The threads 1108 can be configured to engage corresponding threads of a battery storage compartment of sensor electronics module 12 to removably fasten holder 1102 in a battery compartment (not shown) of sensor electronics module 12. Holder 1102 can also include a screw head engagement (not shown) located on a top portion of holder 1102. The screw head engagement can accept a screw driver tip, for example, to facilitate removal of holder 1102 and battery from sensor electronics module 12.

Further to FIGS. 11A and 11B, battery replacement device 1100 can include snap-off handling tab 1110 detachably connected at one end to holder 1102. At its other end, handling tab 1110 can have screw tip 1112. The size of handling tab 1110 can be selected so that a user with reduced dexterity can easily perform both a battery removal and a battery placement operation, as will be described in more detail below.

Battery replacement device 1100 can be used to both remove a battery from a battery storage compartment of sensor electronics module 12 and place a new battery into the battery storage compartment. Screw tip can 1112 be used to engage a corresponding screw engagement section of a battery holder already releasably fixed in sensor electronics module to remove the battery holder and battery contained therein. After the holder and battery is removed, new battery 1104 and holder 1102 at the other end of the replacement device 1100 can be inserted and releasably fixed into sensor electronics module.

Once the holder 1102 is fixed into the housing with the new battery, handling tab 1110 can be snapped off. As illustrated in FIGS. 11A and 11B, frangible sections 1114$a$ and 1114$b$ can be provided on portions of handling tab 1110 that engage holder 1102 to facilitate snapping off of handling tab from holder when a user bends handling tab. Frangible sections 1114$a$ and 1114$b$ can be selected and formed so that handling tab can provide enough force to fix holder 1102 in the sensor electronics module (e.g. by screwing holder into place), but formed so that frangible sections snap off when appropriately bent by a user.

Seal 1106 can also be provided around a periphery of holder 1102, formed, for example, by an overmolding process. In this manner, a new seal, integral with each new holder 1102, can be provided each time a new battery is inserted into sensor electronics module 12. This can facilitate proper sealing of the battery within the housing of sensor electronics module 12 to allow waterproof operation.

Although the embodiment described with respect to FIGS. 11A and 11B uses a threaded engagement mechanism (e.g., threads 1108), holder 1102 can be releasably attached within the housing of sensor electronics module 12 by any suitable connection mechanism. For example, a bayonet-type connection can be used to releasably fix holder 1102 within a battery compartment of sensor electronics module 12.

Temperature Sensor

Some embodiments compensate for temperature changes that may impact performance of sensor 10, such as its sensitivity. In one embodiment, a temperature is measured at the working electrode of sensor 10, where the change of temperature can impact diffusion properties and membrane properties of sensor 10, thus impacting sensitivity. If a temperature or a change in temperature is measured, it can be used to compensate for a change in sensitivity based on a theoretical or a previously characterized relationship. One implementation places a temperature sensor on or in sensor 10 at a working electrode of sensor so that the temperature sensor is placed subcutaneously in a host along with sensor 10. Other implementations can use electrochemistry techniques to measure the temperature at the working electrode, such as use Electrochemical Impedance Spectroscopy (EIS) techniques on the working electrode to determine a temperature at the working electrode.

In another embodiment, a temperature sensor can be placed in mounting unit 240 (FIG. 2B) at a location that is on or near the skin surface of a host. The temperature sensor can be integral with mounting unit 240 and disposed of, along with sensor 10 and mounting unit 240, at the completion of the life of the sensor. The temperature sensor can be in direct contact with the skin, or be coated or potted in a material that has good thermal conductive properties. This material may include the adhesive pad 250. In addition, the temperature sensor (or thermal conductive material) can be surrounded with a thermally insulating material to prevent external temperature changes from impacting the temperature sensing. The temperature sensor can be designed into mounting unit 240 to minimize or eliminate any air gap between the skin and the thermal conductive material or temperature sensor.

Figure 12A:
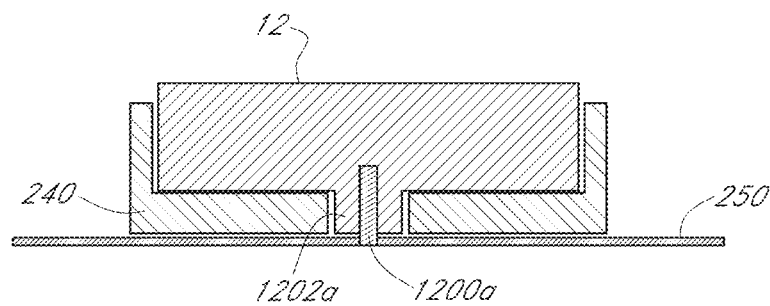
FIGS. 12A, 12B, and 12C are cross-sectional views of different implementations of a sensor system having a temperature sensor in accordance with some embodiments.

In another embodiment, the temperature sensor is an integral component of sensor electronics module 12. To measure as close as possible to the temperature at the working electrode, several implementations can be used, as discussed below. In a first exemplary implementation, a portion of sensor electronics module 12 extends into or next to mounting unit 240 to the skin surface, as illustrated in FIG. 12A. The portion that extends to the skin includes temperature sensor 1200$a$ and thermal insulator material 1202$b$ configured to measure a temperature of a host. Some or all of the insulating concepts discussed above can also be used in this implementation.

Figure 12B:
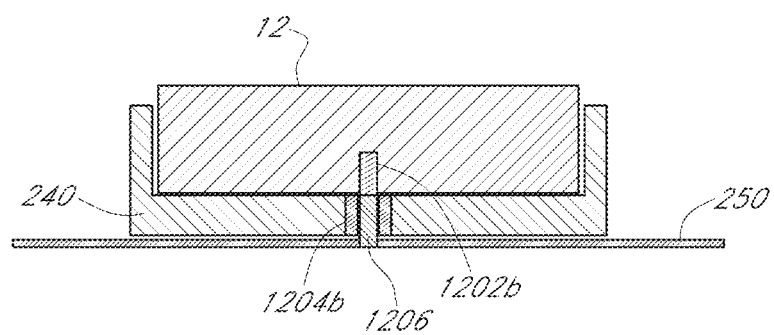

In a second exemplary implementation, a highly thermal conductive material 1206 can be placed in the mounting unit 240 that acts as a thermal conduit to conduct a host's temperature from the skin and/or subcutaneous region of the host to a temperature sensor 1202$b$ located in sensor electronics module 12, as illustrated in FIG. 12B.

In another exemplary implementation, the temperature sensor 1200 is provided on an underside of the adhesive pad 240 or base 242 of mounting unit 240 in the form of a screen printed thick film material that changes resistance as a function of temperature. For example, the material can be printed in the form of a meandering path. By measuring the electric resistance of this meander, the skin temperature can be estimated. An example material that can be used is a carbon particle-based screen printing ink. To increase performance, a paste based on semiconductor particle, like doped silicon, can be used, as this material has a relatively large change in resistance per degree temperature change. A screen printable ink based on small particles (e.g., 1-20 micrometers) can be formulated by suspending the particle in an appropriate binder system (e.g. a polymer based binder in a solvent).

Figure 12C:
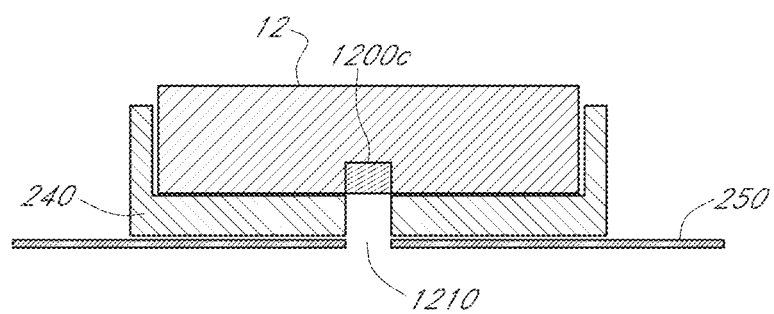

In another embodiment, a temperature sensor measures a temperature of a host's skin without direct contact with a heat measurement component. FIG. 12C illustrates an embodiment wherein infrared temperature sensor 1200$c$ is embedded in an underside of sensor electronics module 12. When sensor electronics module 12 is coupled to mounting unit 240, opening 1210 in the mounting unit 240 aligns with infrared temperature sensor 1200$c$ so an infrared beam generated by temperature sensor 1200$c$ can propagate through opening 1210 onto a host's skin and reflect back to the temperature sensor. The reflected portions of the beam can be detected by sensor 1200$c$, from which the sensor can determine a temperature of the host's skin. The embodiment of FIG. 12C is believed to be beneficial because the temperature sensor 1200$c$ can cause less discomfort to a host and reduce inaccuracy due to irregular contact with the host's skin.

In the embodiment illustrated in FIG. 12C, opening 1210 extends through mounting unit 240 and adhesive patch 250. However, depending upon the composition of adhesive patch 250, the adhesive patch may not significantly affect the temperature measurement of sensor 1208 and, therefore opening 1210 need not extend through the adhesive patch in some embodiments. That is, adhesive patch 250 can extend across opening 1210. Further, some embodiments algorithmically compensate a temperature measurement for a change due to the infrared beam propagating through adhesive patch 250, should the adhesive patch significantly affect the temperature measurement of sensor 1200$c$. In one implementation, a gain factor is applied to a temperature reading to compensate for the infrared beam propagating through the adhesive patch.

In some embodiments, the temperature sensor can 1200 also be used as an indicator that the sensor electronics module 12 is attached to mounting unit 240 and/or that the mounting unit is attached to the skin and/or that the sensor is implanted in the host. For example, if the temperature sensor 1200 or thermal conductor of FIG. 12B is located in the mounting unit 240, sensor electronics module 12 can detect that the sensor electronics unit is attached to the mounting unit when contacts of the sensor electronic module make contact with the temperature sensor or thermal conductor. Similarly, sensor electronics module 12 can be configured to determine that the mounting unit is attached to a host's skin or a sensor implanted in a host by determining that a measured temperature corresponds to the host's body or subcutaneous temperature, for example.

Figure 12D:
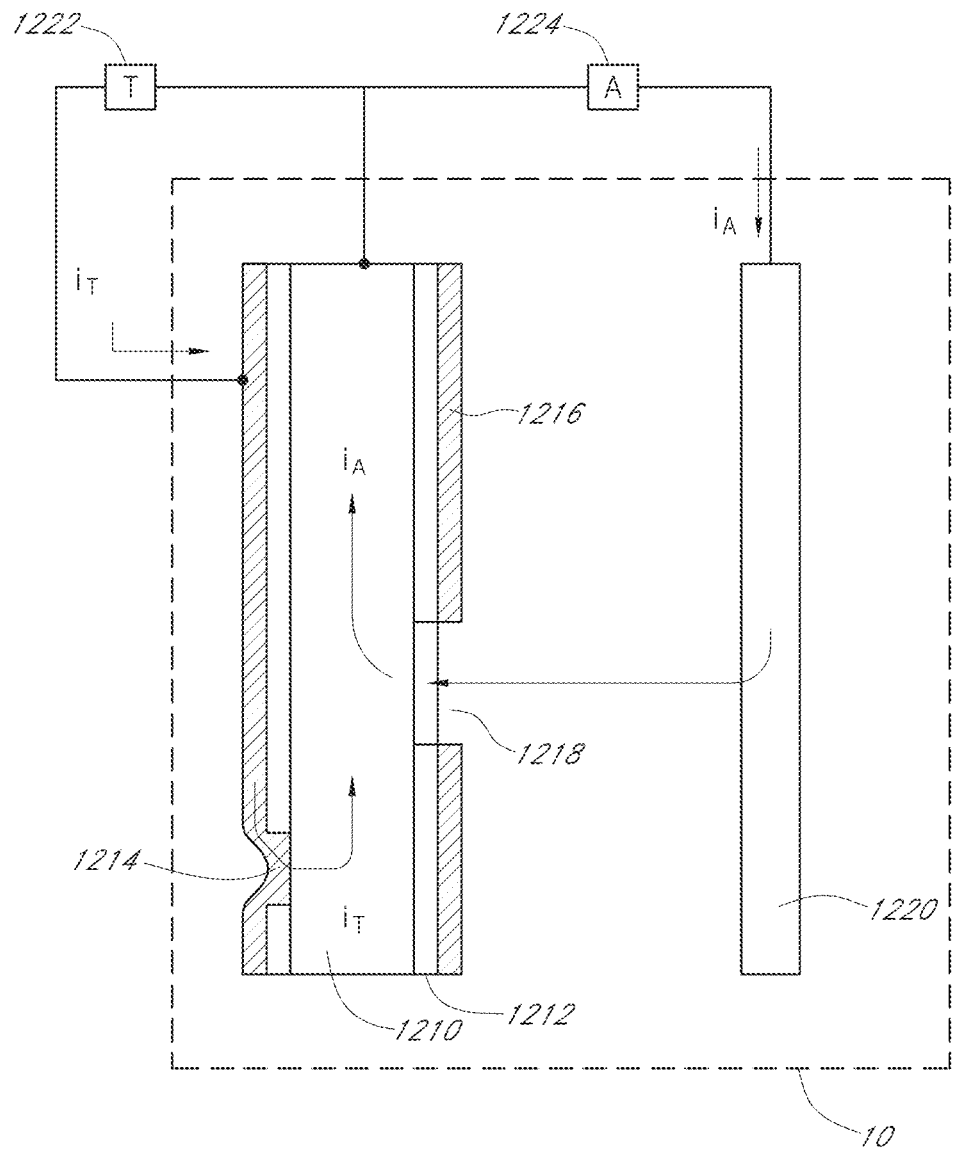
FIG. 12D is a schematic diagram of and implantable sensor with an integrated temperature probe, and associated schematics of components used to measure a temperature and analyte concentration using the sensor, in accordance with one embodiment.

A temperature probe can also be integrated within an implantable analyte sensor tip. FIG. 12D illustrates a partial cross-sectional view of implantable sensor 10 with an integrated temperature probe, and associated schematics of components used to measure a temperature and analyte concentration using sensor 10, in accordance with one embodiment. Here, sensor 10 includes a conductive core 1210, which can comprise platinum clad or tantalum wire. An insulator layer 1212 (e.g., polyurethane) can be coated around the core 1210, having one or more small holes 1214 formed in the insulator layer. The holes 1214 can be formed using laser ablation or photolithography (e.g., by using photo-sensitive polyimide), for example.

Further to FIG. 12D, a conductive layer 1216 is coated over the insulator layer 1212 in such a way that conductive layer 1216 makes electrical contact with the conductive core via hole 1214. The conductive layer 1216 can be applied to sensor 10 using a die based coating process or sputtering, for example. To provide temperature sensitivity, the conductive layer 1216 can consist of or include a conductive material with high resistive temperature coefficient. For instance, a coating paste can be used that comprises a semi-conductive material similar to that used in the manufacturing of thermistors. In the case of sputtering, a thin layer of platinum can be used, because this metal has a relatively high temperature coefficient.

Further to FIG. 12D, a working electrode can be defined using a skive window 1218. The skive window 1218 can be formed using a laser ablation, for example. Skive window 1218 can form an analyte sensitive portion the sensor 10, and an analyte-dependent signal can be obtained by electrically connecting the core 1210 to measurement circuitry 1222 and applying a potential against a reference electrode.

Further to FIG. 12D, temperature measurement circuitry 1222 is used to drive a current $i_T$ through the conductive core 1210 and the outer conductive layer 1216. The current $i_T$ can be a relatively small current, for example in the micro amp range. The potential needed to establish a fixed current $i_T$ through the conductive core 1210 and outer conductive layer 1216 can then be a measure of resistance of the outer conductive layer 1216. This resistance can depend upon temperature and, accordingly, a temperature can be derived from the potential needed to establish a fixed current $i_T$ using a predetermined relationship between temperature and the potential.

Analyte measurement circuitry can be used to drive current $i_A$ passing through external electrode 1220 and conductive core 1210. Current $i_A$ is related to the concentration of analyte (e.g., glucose) in the vicinity of window 1218 when a constant voltage is applied by analyte measurement circuitry 1224. An analyte concentration in the vicinity of window 1218 can then be calculated based on a measurement of current $i_A$. Depending on construction of analyte sensor 10, external electrode 1220 can be a reference electrode in the case of a two-electrode system or a counter electrode in the case of a three-electrode system.

Thus, both temperature and an analyte related-signal can be measured using shared conductor 1210 of sensor 10. Additionally, in some embodiments, temperature and the analyte-related signal can be measured at the same time using the configuration illustrated in FIG. 12D.

In some embodiments, an algorithm is used to adjust sensitivity of analyte sensor 10 based on an absolute temperature or change in temperature. In general terms, the sensitivity can change according to Ficks law, at about 3% per degree Celsius. The relationship can be measured empirically and an equation derived to adjust a sensitivity of analyte sensor. The adjusted sensitivity can then be used to calculate analyte concentration values using data generated by analyte sensor 10, for example.

Temperature can also impact other parameters affecting measurement of analyte sensor 10, such as run time, time lag, baseline, etc. of the analyte sensor. Information on temperature can be used to adjust an algorithm or one or more the aforementioned parameters, and analyte concentrations can be calculated using the adjusted algorithm and/or parameters.

An example is a run-in time of sensor 10 may increase as the temperature of the sensor decreases at startup. Based on a predetermined relationship between temperature run-time, an algorithm can then be used to adjust the run in time accordingly. Additionally, certain failsafe parameters in an algorithm can be impacted by the temperature such as maximum baseline, minimum sensitivity, and upper and lower "acceptability" boundaries. These parameters can also be modified according to the temperature or temperature change. Upper and lower "acceptability" boundaries are discussed in more detail in U.S. Patent Publication No. US-2006-0222566-A1, the entire content of which is incorporated herein by reference. The algorithm can be in the form of software executable by a microprocessor of sensor electronics module 12 or a display device 14, 16, 18 or 20, for example.

The temperature information can also be used as an indicator for other biological activity, such as local infection, hypoglycemia, physical activity or exercise, etc., and this information can be used to trigger alerts, initiate algorithm adjustments, or be used in calculations such as energy expenditure.

In some embodiments, a heating element can also be included in sensor system 8. In general, heating element can be used to elevate the temperature in proximity to sensor 10 to improve perfusion of blood and/or other subcutaneous fluid to sensor 10. The heating element can improve sensor performance by providing a more consistent temperature to the sensor site, reducing temperature fluctuation errors in sensor readings. The heating element can be positioned in vivo or ex vivo during use of sensor 8. Further, the temperature in proximity to the sensor site can be passively or actively controlled by sensor system 8 using the hearing element. In some embodiments, a temperature is measured using temperature sensor 252 and heating element is controlled by sensor system 8 based on the measured temperature to keep the temperature at the sensor site within a predetermined range of temperatures. In one embodiment, the heating element comprises an electrical element that emits heat based on current flowing through the element, such as a known coiled wire heating element. Alternatively, heat can be applied to the sensor site using ultrasound emitted by a transducer included in sensor system 8.

Compression Sensor

Embodiments of glucose monitoring systems disclosed herein can not only monitor a patient's glucose values, but also alert the patient for trends in the monitored glucose readings, such as alerting the patient for actual or impending hypoglycemia, for example. As discussed herein, these alerts can be accomplished by vibratory or audible alarms. If the alarms are correct and accurately represent true glucose in the body, these alerts can prevent serious hypoglycemic episodes leading to unconsciousness or death. However, if these alarms are incorrect, and erroneously warn the patient of hypoglycemia when the actual blood sugar is in the normal range, the alarms will be rightfully perceived by the patient as annoyance and inconvenience. In the event of frequent alarms, a phenomenon described as "alarm fatigue" can occur in which will ignore correct potentially life-saving alerts because of their previous experience with annoying erroneous alerts.

In addition, embodiments of glucose monitoring systems disclosed herein can be used as part of an automated insulin infusion system or artificial pancreas system. Some embodiments can be configured to automatically suspension of insulin infusion in response to detected actual or impending hypoglycemia. As above, if the detection of hypoglycemia is correct, such an insulin pump suspension could be lifesaving. However, if the hypoglycemia detected by the sensors is erroneous, there is the risk that an automatic pump suspension could lead to severe hyperglycemia, possibly culminating in diabetic ketoacidosis.

Although not wishing to be bound by theory, it is believed that some analyte sensors, such as continuous glucose sensors, can become inaccurate when the tissue in proximity to the sensor is compressed. In the example of an implanted glucose oxidase-based sensor, for example, it is believed that compression of the tissue in proximity to the sensor can cause reduced perfusion of glucose and/or oxygen to the sensor. Consequently, a resulting sensor output may not be indicative of a patient's overall glucose concentration level, leading to the glucose monitoring system potentially outputting inaccurate information, for example. That is, the output signal may be substantially reduced during the time of compression in proximity to the sensor, resulting in erroneously low sensor readings and possibly triggering false alerts.

One possible cause of compression in the proximity of the sensor can be when a user sleeps on the sensor system 10, because the user's body presses sensor system 10 against the user's tissue in proximity to the implanted sensor 10.

Compression can last for a period of time such as 5 to 60 minutes, several hours or even longer. Accuracy can return when the patient adjusts positions and no longer compresses the sensor.

As illustrated in FIG. 2A, sensor electronics module 12 can include compression sensor 254. Compression sensor 254 can indicate if tissue is being compressed in proximity to sensor 10. Compression sensor can be configured to detect a magnitude of force applied to sensor electronics module 12, and sensor electronics module can initiate one or more actions in responsive to the detected force. The initiated actions can include: (i) triggering an alert, such as a userperceptible audible or tactile alarm; (ii) suspending or modifying a medication administration routine, such as insulin in the case of the sensor system being part of an automated insulin infusion system or artificial pancreas system; (iii) suspend display of data on a display device; (iv) modify or apply a different algorithm to data measured using sensor 10 based on a level of the detected force.

In accordance with some embodiments, compression sensor 254 comprises a pressure sensor, such as a miniature piezo-electric pressure transducer. As discussed above, a user pressing the sensor system 10 against an object, such as a bed while sleeping, can cause tissue to compress in proximity to an implanted sensor of the sensor system. The compression of tissue can lead to erroneous readings of the implanted sensor. Accordingly, the pressure sensor can be configured to measure a pressure applied against sensor system, which can indicate compression of tissue in proximity to the implanted sensor. Some embodiments can be configured to measure both lateral forces and longitudinal forces applied against the sensor system 10, while other embodiments can be configured to only measure lateral or longitudinal forces applied against the sensor system.

Figure 13:
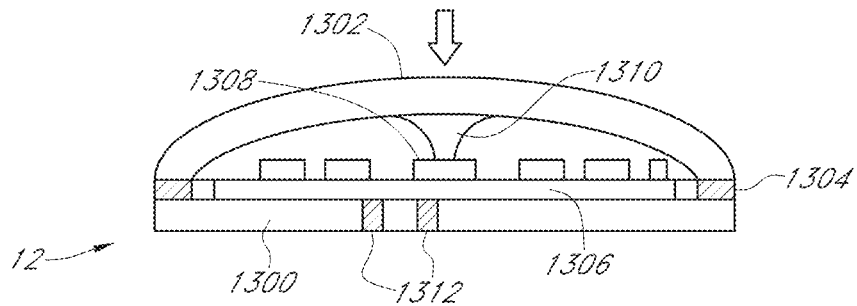
FIG. 13 illustrates a first embodiment of sensor electronics module including a pressure sensor configured to detect compression in proximity to an implanted sensor.

FIG. 13 illustrates a first embodiment of sensor electronics module 12 including a pressure sensor configured to detect compression in proximity to an implanted sensor. Here, an outside housing of sensor electronics module 12 can include a rigid base 1300, a rigid cover 1302 and a compressible gasket 1304 between the base and cover. The housing can define an interior portion in which a printed circuit board (PCB) 1306 is carried on the interior portion of the base 1300. The PCB 1306 can incorporate ASIC 205 of FIG. 2A, for example. A pressure sensor 1408 resides on PCB 1306 and a contact 1310 resides on an interior portion of cover 1302. Contacts 1312 extend through base 1300 and are electrically coupled to PCB 1308 so that PCB can be electrically coupled to sensor 10 and/or electronics of mounting unit 240, for example.

In use, a sufficient external force applied to cover 1302 (e.g., a force applied in a direction perpendicular to the base 1300) can cause contact 1310 to apply pressure on pressure sensor 1308 due to use of compressible gasket 1304. Pressure sensor 1308 can then measure the applied and output data indicative of the measured force PCB 1306 for processing and/or initiating one or more actions in the manned described above.

Figure 14:
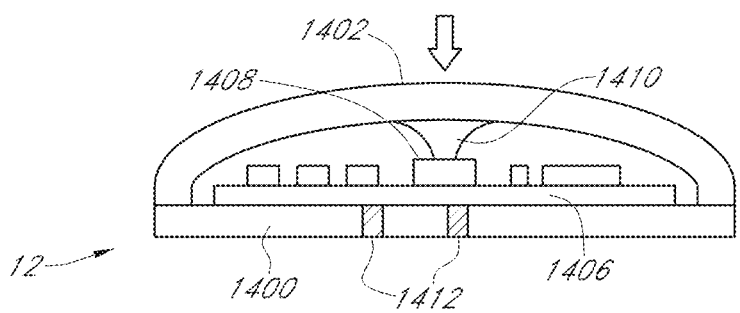
FIG. 14 illustrates a second embodiment of sensor electronics module including a pressure sensor configured to detect compression in proximity to an implanted sensor.

FIG. 14 illustrates a second embodiment of sensor electronics module 12 including a pressure sensor configured to detect compression in proximity to an implanted sensor. The second embodiment is similar to the first embodiment cover 1402 is compressive instead of rigid like cover 1302. Further, because the cover 1402 is compressive, compressible gaskets 1304 are not included in the second embodiment. Base 1400, PCB 1406, pressure sensor 1408 contact 1410 and contacts 1412 can be the same as base 1300, PCB 1306, pressure sensor 1308 contact 1310 and contacts 1312, respectively.

The second embodiment can also measure sufficient externally applied force to cover 1402. An exemplary detected force is illustrated as an arrow in FIG. 14. Pressure sensor 1408 can then measure the applied and output data indicative of the measured force PCB 1406 for processing and/or initiating one or more actions in the manned described above.

Note that the first and second embodiments include compression sensor 254 in sensor electronics unit 12. It is understood that a pressure sensor can instead or additionally be placed in another component of sensor system 8, such as in a mounting unit configured to hold sensor 10 and sensor electronics unit 12. In such an embodiment, the mounting unit can include a compressible portion of the housing of the mounting unit and the pressure sensor can be configured to measure a force applied to the compressible portion of the housing and output data representative of the detected force to sensor electronics unit 12.

In some embodiments, sensor system 8 is designed to give the patient discomfort if the patient is compressing the sensor. In one embodiment, the sensor system 8 has a housing shaped to provide discomfort to the host if pressure is applied to the sensor system. For example, an underside of mounting unit 240 can be shaped having a protrusion that provides discomfort should a host apply a pressure against the sensor system 8. In another embodiment, sensor system 8 can apply a mild electrical shock to host should compression sensor 254 measure more than a predetermined amount of pressure.

Splitable Pod

In some situations, a user may not want to carry a separate display device. However, the user may still need to or want to check sensor reading levels. Some embodiments enable the host to be more discreet in his or her diabetes management while still allowing him or her to collect sensor data as usual. In one embodiment, a continuous analyte monitoring system is configured with a split able pod, which contains both sensor electronics module 12 and a splitable display unit incorporating some or all of the features of display device 14, for example. The entire splitable pod can be attached to mounting unit 240, for example. An additional display unit may also be used, such as display device 16, 18, or 20, depending upon the user's preference and/or system configuration.

In some embodiments, the splitable display unit is about the size of a credit card, configured to dock on sensor electronics module 12, and configured to make a direct electrical connection with the sensor electronics module 12. While splitable display unit is docked on the sensor electronics module 12, the splitable display unit can be configured to continuously collect/process/store data. When the host wants to check his or her glucose reading, he or she disconnects splitable display unit from the sensor electronics module 12 and looks at the display. The user can thereafter dock splitable display unit to the sensor electronics module 12 when he or she is done looking at the display (or optionally calibrating the system). Thus, in such an embodiment, neither the sensor electronics module nor splitable display unit need wireless communication capabilities, although one or both units can have wireless communication capabilities if so desired.

In some embodiments, the sensor electronics module 12 has a disposable battery to maintain a potential at the electrodes during the time the splitable display unit is disconnected from the sensor electronics module. However, in other embodiments, the splitable display unit is the sole power source for the sensor electronics module and sensor. When the splitable display unit is the sole source of power, the sensor electronics module can include capacitive circuitry that charges while the splitable display unit is docked to the sensor electronics unit, and switches from charging to providing power to one or more components of the sensor electronics module when the splitable display unit is disconnected.

In some embodiments, sensor system includes a two-part display unit having a smaller part and a larger part. The smaller part of the displayable unit can be configured to be small enough for a user can carry all times and can include a display capable of showing a current glucose value and a trend arrow, for example. The smaller part can also be configured with an alarm and/or to store glucose information throughout a period of time for retrieval when interfaced with the second part of the display unit or another computer device, such as a PC. In addition, the smaller part can include a telemetry module, such that it can be worn on the body of a user and transmit and/or receive data.

A larger part can be configured with a screen similar to that of the display device 16. The larger part can be docked with the smaller part, to receive the glucose values and provide graphing capabilities and additional data analysis such as statistics. It is through the larger part that settings (e.g., alerts & alarms and date & time) can be set by the user and/or a caretaker and/or the manufacturer. Additionally, an interface with a PC can be achieved through the larger part.

Depending upon personal preference and/or need, the user can elect to carry both parts with him for the full functionality. Alternatively, the user can elect to carry only the smaller part, in order to be less inconvenienced by the size of the larger unit or to have sensor capability in a discreet manner knowing that the glucose values will be stored for future visibility and analysis.

In some embodiments, the splitable pod can contain disposable elements of sensor electronics module in one part and reusable elements of sensor electronics module in the other part. The selection of disposable and reusable elements can be based on whether a new user should use the reusable part of the splitable pod. As an illustrative example, it may be desired to allow a first user to use sensor electronics module during a first time period and then have a second user use the sensor electronics module during a later, second time period. Should personal, private information be stored in the sensor electronics module, then the splitable pod can be configured so that the personal, private information is only stored in memory located in the disposable part and reusable information, such as sensor diagnostics software, is stored in memory located in the reusable part.

Figure 15:
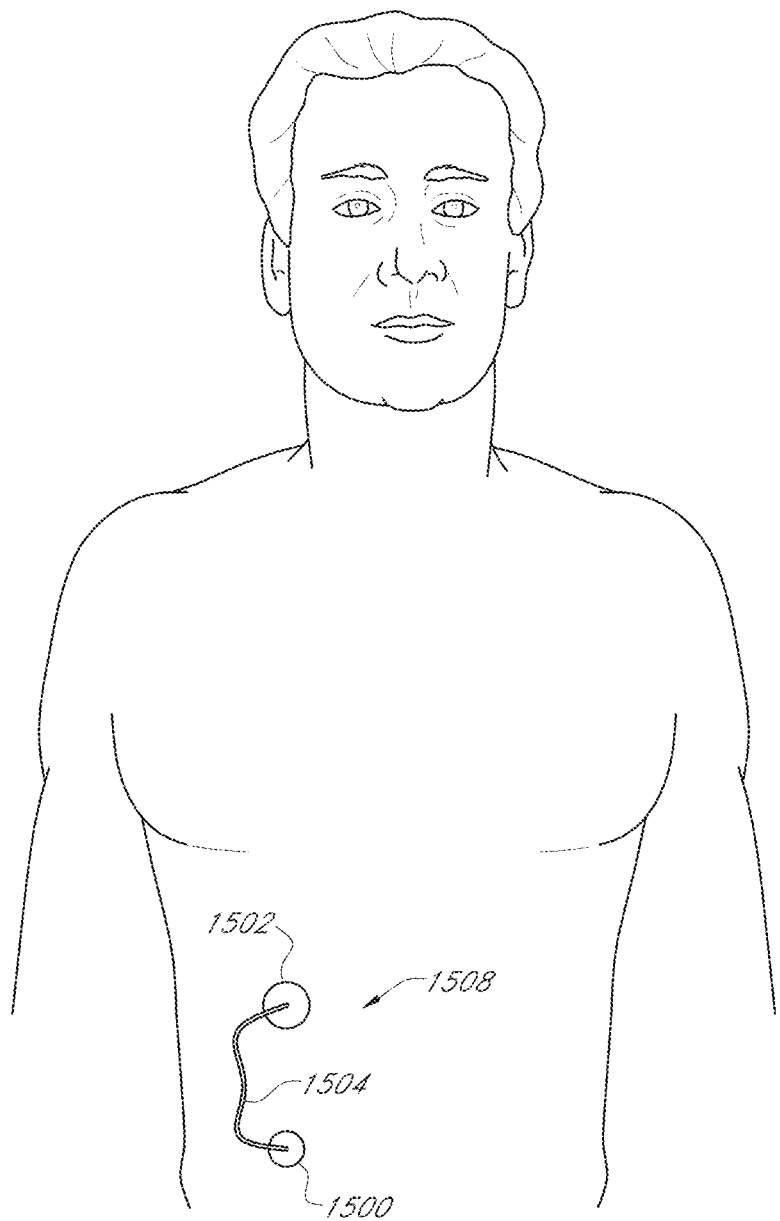
FIG. 15 illustrates a splitable pod sensor system in accordance with one embodiment.

FIG. 15 illustrates an embodiment of sensor system 1508 with physically separate parts 1500 and 1502 connected to one another via a wire tether. As discussed above, some embodiments utilize a sensor electronics module that is physically attached to a sensor mounting unit. However, such a configuration can be bulky if both the sensor electronics module and mounting units are large in size, for example. By separating components of the electronics sensor module and the mounting unit between separate parts 1500 and 1502, sensor system 1308 need not be so constrained in size. In some embodiments, the first part 15300 includes most or all of the electrical components in mounting unit 240, including sensor 10, and second part 1502 includes most or all of the electrical components of sensor electronics module 12. However, in other embodiments, the first part 1500 can contain some of the electronics components contained in sensor electronics module 12 instead of second part 1502, such as a potentiostat.

Further, first part 1500 and second part 1502 of sensor system 1508 can each be placed at an optimum location on a user. For example, the first part 1500, containing sensor 10, can be placed on the body at an optimal location to sense desired bodily characteristics, such as the user's abdomen. The second part 1502, containing, for example, telemetry module 232 can be placed on the user's body at another location that is comfortable for the user, such as the user's chest.

Sensor Insertion Detector

Some embodiments can detect inaccuracies in sensor readings caused by an implantable sensor, such as sensor 10, not being implanted to a sufficient depth in a host. Upon a detection of insufficient depth, sensor embodiments can trigger an alert and/or enter a different mode of operation, such as a fail-safe mode or power down mode.

Failures of a sensor can arise when the sensor is pulled out of a host during the sensor's use (i.e. while the sensor is implanted in a host) or if the sensor is not implanted to a sufficient depth. As it gets pulled out, less than a sufficient amount of a sensor may remain in the host, resulting in inaccurate sensor readings, for example. Further, in some embodiments, sensor 10 has a membrane that needs to hydrate in a host's body after implantation, before the sensor provides accurate readings. Should the sensor not be sufficiently implanted into a host during sensor insertion, however, sensor 10 may only partially hydrate, creating non-glucose related signals that can cause inaccuracies in the sensor readings.

To detect inaccuracies caused by insufficient insertion depth and/or sensor pull out, some embodiments include one or more detectors configured to detect whether the sensor is inserted to a proper depth.

In some embodiments, the sensor includes a sensor depth detector. As discussed above, some embodiments of a sensor 10 include a portion that is implanted in vivo a portion that remains ex vivo during use. Thus, the detector can be located on an in vivo portion of the sensor in accordance with one embodiment. For example, the detector can be located at a point along the length of the sensor at which the sensor should be placed subcutaneously in a host when properly implanted. In this manner, if the detector detects that it is not in vivo, then the sensor system can determine that the sensor is not implanted to a sufficient depth.

In one embodiment, an extruded design is used, including but not limited to an extruded wire sensor having multiple concentric electrodes positioned along the length of the wire. Suitable extruded sensor designs are discussed in more detail in U.S. patent Ser. No. 12/829,296, entitled "Analyte Sensors and Methods of Manufacturing Same," and filed on Jul. 1, 2010, the entire content of which is incorporated herein by reference. A sensor depth detector can reside at a point on the sensor just below where the sensor should interface a host's skin when the sensor is properly implanted into the host. The sensor detector can then detect if the sensor detector is not positioned the host. As one example, the detector can be implemented using impedance measurements to determine whether or not the detector is implanted in the host's body. For example, the resistance (e.g., impedance) of a detector may change depending upon whether the detector is located in a host's tissue. Thus, the detector can measure a resistance to determine whether the sensor detector is located in a host's tissue, similar to measuring a temperature, as discussed above. Alternatively, the detector can use measurement techniques that measure electrochemical properties of the sensor, measure a spectrum of impedances of the sensor (using EIS, for example), measure optical characteristics of the sensor, or the like, to determine whether or not the detector is implanted in the host's body.

In one embodiment, the insertion depth of sensor 10 can be determined based on a measurement of a surface area of the sensor using an electrode of the sensor. The reference electrode can be used to make this measurement; although a working electrode, a counter electrode or a specific depth detection electrode can be used instead. In addition, an array or combination of any of these electrodes can be used to measure the electrochemical surface area. The electrode or electrodes used to make the measurement can run continuously along the length of the sensor or periodically along the length of the sensor.

As a non-limiting example, the insertion depth can be measured by sensing the surface area of an active electrode. In some embodiments, only wetted portions of the electrodes are active and only the portion of the sensor that is under the skin remains wet. Therefore, a measurement of the electrode surface area can be proportional to the depth of insertion. Methods of measuring the surface area can be based in whole or in part on an estimate the capacitance of the electrode using techniques such as voltammetry, chronopotentiometry, current step and potential step, differential chronopotentiometry and the like. Other techniques that can be used identify oxygen absorption rates using potential/current sweep or pulse methods.

Switching Display Mode of CGM Data Based on Discordant BG Meter Data

Some embodiments also address problems of discordant continuous glucose monitoring (CGM) data and blood glucose (BG) meter data that are not due to error in either instrument. Some embodiments of CGM sensors measure glucose in the interstitial space of a user, such as in the abdomen of the user. BG meters typically measure glucose from capillary whole blood, such as from the fingertip of a user. Measurements from both CGM and BG meter may be accurate, but because the instruments measure from different body fluids and different locations, the measurements reflect actual difference in glucose testing concentration, which can be referred to as "compartment effect" (data collected from alternate sites, for example, suggest that changes in blood glucose after a meal show the finger stick sites before forearm or thigh sites: Ellison et al., Diabetes Care 25:6, 2002). If a BG meter value is taken at a time when the blood glucose and interstitial glucose concentrations differ, and the value is entered for CGM calibration, the difference in measurements can cause inaccuracy because the correlation of the CGM signal to BG has transiently changed.

In one embodiment, when the system concludes that a confidence level of CGM data is high and that CGM data is discordant from BG meter calibration value, the system can be configured to ignore the BG meter calibration value. Determining a confidence level and discordant data is discussed in more detail in U.S. Patent Publication No. US-2005-0043598-A1, the contents of which are hereby incorporated by reference in its entirety. In such a situation, the system may be configured to cause the system to be non-responsive to BG meter data inputs. However, this can cause confusion or frustration for the user.

An embodiment enters a different state if the likelihood of "compartment effect" is high. In this state, the system accepts BG meter value, but does not use the BG value for calibration. Further, a display changes to a state that displays different information than that of the prior state. For example, in a first state, a glucose trend graph and a glucose value are shown on the display. This first state can be referred to as a "calibrated" state. However, in a second state—which is shown if the likelihood of compartment effect is determined to be high—the display can continue to display a glucose trend graph, but does not display a glucose value. This second state can be referred to as a "trend only" state. Alternatively, the system can display a glucose value in the second state, but the system may require additional keystrokes or other inputs from a user prior to displaying the value to ensure the user realizes that the likelihood of compartment effect is high. By not displaying the value, a trend only state is visibly different from a calibrated state.

To exit a trend only state, one or more of the following events can occur: the sensor system determines that the likelihood of compartment effect is low; or a second BG value is entered into the sensor system that confirms the accuracy of the CGM data. Depending on the likelihood of compartment effect, if the BG and CGM data remain discordant, the system may switch from the calibrated state to the trend only state.

Quality/Accuracy Indicators of Data

Some embodiments of a continuous analyte monitoring system measure an electrical current indicative of an analyte concentration process the current measurements through a calibration algorithm and present the data without additional knowledge of the quality or accuracy of the data being presented.

However, some embodiments of a continuous analyte monitoring system add self diagnostics and error checking sensors, and/or algorithms to produce metrics of data quality. Sensors that can measure such metrics include: automated drift detection, moisture ingress, temperature, day of use of sensor, low oxygen detection, end of life, rapid rates of change, poor circulation (due to compression of tissue around the sensor site, for example), inaccuracies during start up time, long start up time, instability or noise in the signal, etc.

One metric can include observing error during rapid rates of change. The error can be caused by time lag of the sensor site or compartment effect, for example. The analyte monitoring system may be discordant from blood glucose (BG) meter data during these rapid rates of change. This error can be mitigated by utilizing the rate specific information as an additional metric that indicates accuracy.

In some embodiments, the data from these metrics can be used as individual triggers for one of a plurality of actions or combined into a universal quality score and one of a plurality of actions can be triggered based on the quality score. The actions taken based on the individual metrics or universal quality score can include one or more of: stop displaying data, display a trend and arrow only, an indicator that indicates when the data can be used for a therapeutic decision or for track and trend information only, display a range instead of a value (or error bars on the value), determine if a calibration point should be requested or accepted, an importance level or weight for calibration point into the algorithm, a metric that can be used in closed loop systems to go into a safe insulin does rate, stop insulin dosing or adjust the dosing to ensure safety, or a combination of any thereof.

Accordingly, some embodiments of a continuous analyte monitoring system include self diagnostic capabilities to analyze quality or accuracy of the data being generated based on the metrics of data quality, such as the metrics discussed above. The quality or accuracy analysis can then be used to change a display, such as a display on display device 14, 16, 18 or 20 (FIG. 1), to indicate performance, or can be used to impact feedback control algorithms for closed loop systems. The quality or accuracy analysis can be important to ensure quality of the data being displayed, particularly in closed loop analyte monitoring and treatment systems, for example.

Figure 16:
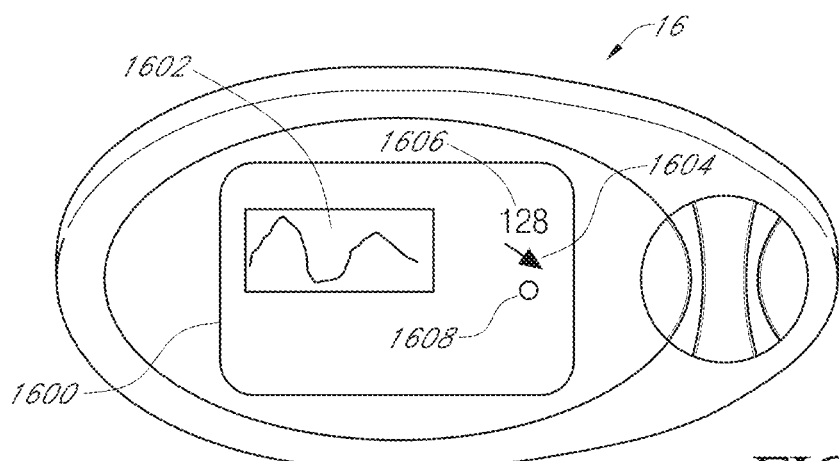
FIG. 16 illustrates a display device having a quality indicator in accordance with one embodiment.

FIG. 16 illustrates a display 1600 of display device 16 in accordance with one embodiment. Here, display 1600 can display a variety of glucose sensing related information, including trend graph 1602, trend arrow 1604 and numerical value of glucose concentration 1606. Display 1600 also includes accuracy/quality indicator 1608. Depending upon a quality metric based on an analysis of quality or accuracy of the data being generated, accuracy/quality indicator 1608 can change between one of a plurality of states, such as changing color, flashing or turn off and on. Various quality metric thresholds can be used to determine the state in which accuracy/quality indicator 1608 is displayed.

Figure 17A:
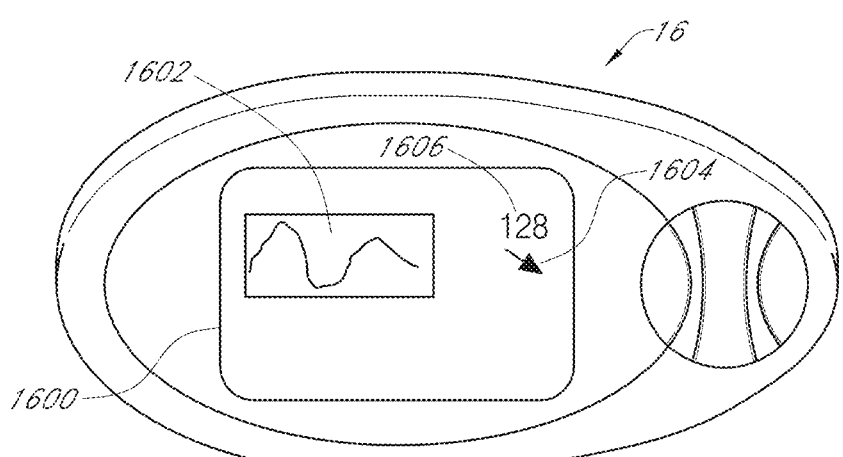
FIGS. 17A and 17B illustrate a display device that is configured to display information based on a quality metric in accordance with one embodiment.
Figure 17B:
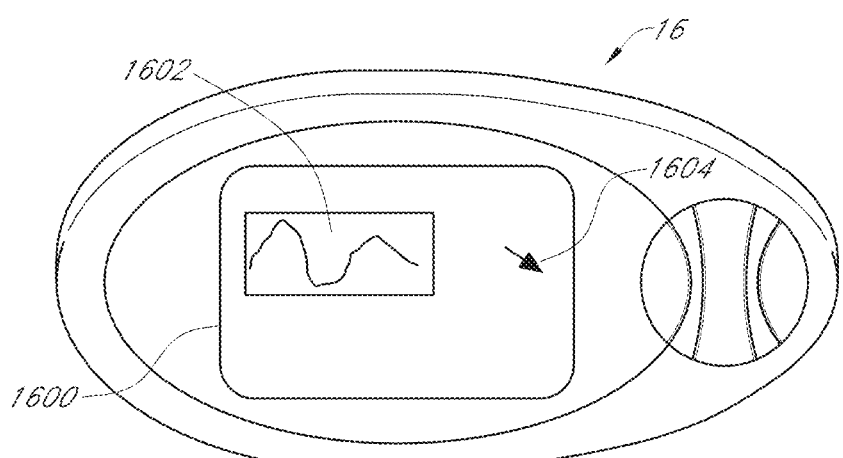

FIGS. 17A and 17B illustrate a display 1600 of display device 16 in accordance with one embodiment. Here, FIG. 17A shows display 1600 in a first display state and FIG. 17B shows display 1600 in a second display state. The display states can be triggered by a quality metric. If the quality metric is above a threshold, display 1600 shows the first display state that can be considered therapeutically accurate. The first display state can include displaying a trend graph 1602, trend arrow 1604 and a numerical glucose value 1606. If the quality metric is below a threshold, the display shows a second display state that can be considered "track and trend" accurate. The second display state can include displaying trend graph 1602 and trend arrow 1604, but not a numerical glucose value.

Figure 18A:
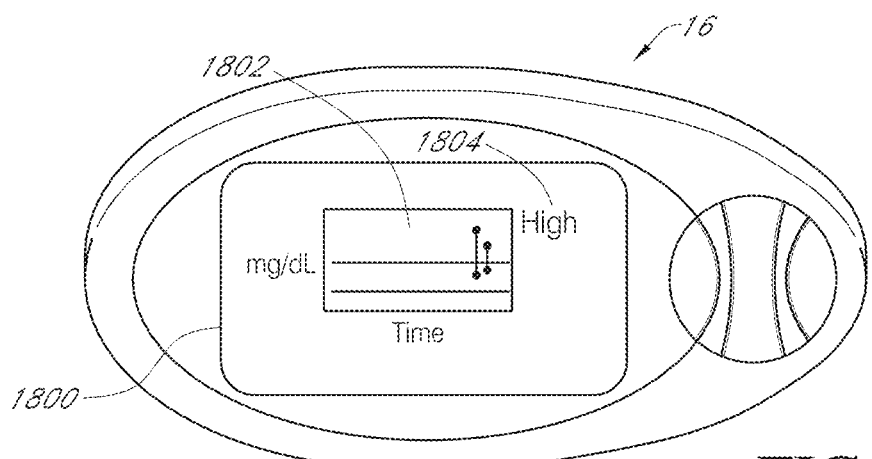
FIGS. 18A, 18B, and 18C illustrate displays showing ranges of possible values in accordance with one embodiment.
Figure 18B:
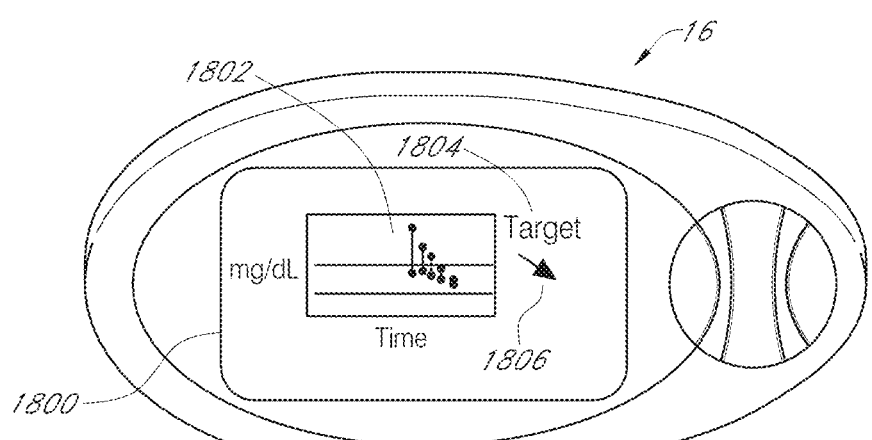
Figure 18C:
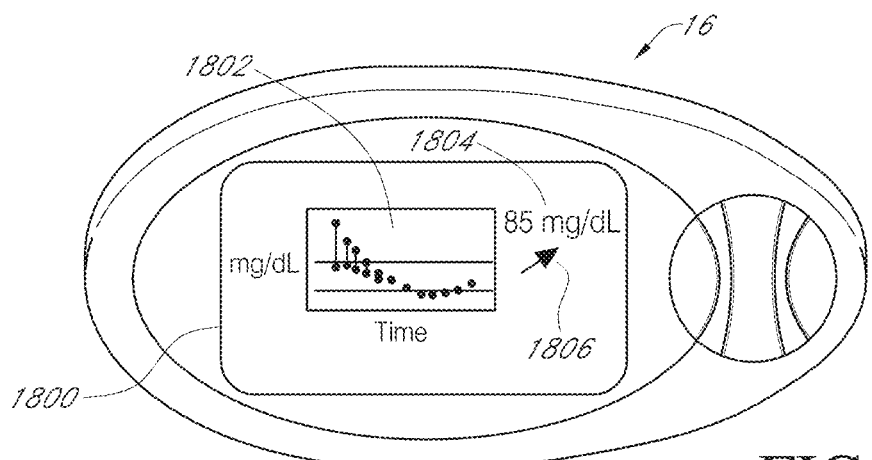

FIGS. 18A-18C illustrate displays showing ranges of possible values in accordance with one embodiment. Here, display 1800 includes a trend graph 1802, wherein the trend graph displays ranges of glucose data. The ranges can be indicative of an accuracy of each data point. As the data becomes more accurate, the ranges narrow, as best illustrated in FIG. 18C. The accuracies can narrow due to sensor metrics configuring accuracy or a calibration point is taken, for example.

Further to FIGS. 18A-18C, the display 1800 can change display states depending upon the accuracy of the data. FIG. 18A is display 1800 in a first state where the data is accuracy is low. Here, display 1800 only includes a trend graph and an indicator 1804 that the analyte ranges fall within a high threshold level. FIG. 18B illustrates display 1800 in a second state where the data accuracy is intermediate. Here, the display 1800 displays the trend graph 1802, an indicator 1804 to indicate that the analyte ranges fall within a target range. In addition, the display includes a trend arrow 1806. FIG. 18C illustrates the display 1800 is a third state. Here, because the ranges are narrow, the display 1800 includes indicator 1804 to indicate a numerical analyte concentration value.

In some embodiments, the continuous analyte monitoring system is also configured to calculate and transmit two values. One value is used for display to user on one of the display devices 14, 16, 18 or 20, for example. The second value is used for treatment devices, such as insulin dispensing pen or pump. In one embodiment, the value sent to user represents a closest value of actual analyte concentration based on system metrics used to calculate the concentration. The value sent to the dispensing unit, for example an insulin dispensing pump, is a value that is derived based on weighted clinical factors, etc., such that use of the value is least likely to cause a user to go into a dangerous health condition, such as a hypoglycemic state in the example of diabetes.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An analyte monitoring system comprising:
an analyte sensor;
a display device; and
a sensor electronics module comprising:
   a battery;
   a microprocessor;
   sensor measurement circuitry coupled or couplable to the analyte sensor; and
   a telemetry module configured to wirelessly communicate displayable sensor information to the display device; and a capacitor, wherein:
the sensor electronics module is configured to selectively operate in:
a shelf mode during storage of the sensor electronics module prior to a sensor session,
a first power mode in which a voltage is configured to be applied to the analyte sensor and in which the sensor measurement circuitry is configured to not perform any analyte sensor measurements, and
a second power mode in which the voltage is configured to be applied to the analyte sensor and in which the sensor measurement circuitry is configured to perform at least one analyte sensor measurement;
the battery is configured to:
apply the voltage to the analyte sensor system in the second power mode, and
recharge the capacitor in the second power mode;
the capacitor is configured to:
apply the voltage to the analyte sensor in the first power mode, and
recharge in the second power mode; and
the sensor electronics module is further configured to:
transition from the shelf mode to the first power mode in response to an interrupt signal indicating that the sensor session is being initiated,
transition from the first power mode to the second power mode in response to an enable signal from the microprocessor provided after a stabilization time period, and
transition from the second power mode to the first power mode based on completion of at least one sensor measurement and after the capacitor has been recharged.

2. The analyte monitoring system of claim 1, wherein the sensor electronics module is configured to perform the at least one analyte sensor measurement when in the second power mode.

3. The analyte monitoring system of claim 2, wherein the sensor electronics module is configured to periodically perform the at least one analyte sensor measurement in the second power mode.

4. The analyte monitoring system of claim 1, further comprising a switch connected between the battery and both the sensor measurement circuitry and the telemetry module.

5. The analyte monitoring system of claim 1, wherein the sensor measurement circuitry comprises operational amplifiers.

6. The analyte monitoring system of claim 1, wherein the voltage is a constant voltage.

7. A system for measurement of an analyte in a host, the system comprising:
an analyte sensor; and
a sensor electronics module coupled to or couplable to the analyte sensor, the sensor electronics module comprising:
a battery;
a capacitor;
sensor measurement circuitry;
a telemetry module;
a switch configured to switch the sensor electronics module out of a shelf mode implemented during storage of the sensor electronics module prior to a sensor session; and
a switch configured to switch the sensor electronics module between a first power mode and a second power mode different from the first power mode, wherein:
the second power mode consumes more power than the first power mode;
in the first power mode:
a voltage is configured to be applied to the analyte sensor; and
the sensor measurement circuitry is configured to not perform and analyte sensor measurements;
in the second power mode:
the voltage is configured to be applied to the analyte sensor; and
the sensor measurement circuitry is configured to perform at least one analyte sensor measurement;
the battery is configured to:
apply the voltage to the analyte sensor system in the second power mode, and
recharge the capacitor in the second power mode;
the capacitor is configured to:
apply the voltage to the analyte sensor in the first power mode, and
recharge in the second power mode; and
the sensor electronics module is configured to:
transition from the shelf mode to the first power mode in response to an interrupt signal indicating that the sensor session is being initiated,
transition from the first power mode to the second power mode in response to a microprocessor enable signal provided after a stabilization time period, and
transition from the second power mode to the first power mode based on completion of at least one sensor measurement and after the capacitor has been recharged.

8. The system of claim 7, further comprising a display device.

9. The system of claim 8, wherein the sensor electronics module is configured to transmit the sensor information to the display device using at least one wireless communication protocol.

10. The system of claim 7, wherein the sensor voltage is a constant voltage.

11. The system of claim 7, wherein the sensor electronics module is configured to periodically perform the at least one analyte sensor measurement in the second power mode.

* * * * *